United States Patent
Nagarathnam et al.

(10) Patent No.: US 6,172,066 B1
(45) Date of Patent: *Jan. 9, 2001

(54) DIHYDROPYRIMIDINES AND USES THEREOF

(75) Inventors: Dhanapalan Nagarathnam, Ramsey; Wai C. Wong, Newark; Shou Wu Miao, Edison, all of NJ (US); Michael A. Patane, Harleysville, PA (US); Charles Gluchowski, Danville, CA (US)

(73) Assignee: Synaptic Pharmaceutical Corporation, Paramus, NJ (US)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/858,061

(22) Filed: May 16, 1997

Related U.S. Application Data

(60) Provisional application No. 60/017,582, filed on May 16, 1996.

(51) Int. Cl.$^7$ ............... A61K 31/497; A61K 31/506; A61K 31/505; C07D 239/32

(52) U.S. Cl. ............... 514/252; 514/256; 514/269; 514/272; 514/274; 514/275; 514/258; 544/295; 544/310; 544/311; 544/312; 544/316; 544/317; 544/319; 544/321; 544/322; 544/324; 544/325; 544/333; 544/278; 544/279; 544/280

(58) Field of Search ............... 544/317, 316, 544/333, 310, 311, 312, 319, 321, 322, 324, 325, 295; 514/274, 269, 275, 252, 272, 256

(56) References Cited

U.S. PATENT DOCUMENTS

| | | | |
|---|---|---|---|
| 4,438,117 | 3/1984 | Cherkofsky | 424/251 |
| 4,684,653 | 8/1987 | Taylor et al. | 544/279 |
| 4,684,655 * | 8/1987 | Atwal | 514/274 |
| 4,684,656 | 8/1987 | Atwal | 544/316 |
| 4,703,120 | 10/1987 | Press | 544/278 |
| 4,728,652 * | 3/1988 | Atwal | 514/274 |
| 4,845,216 | 7/1989 | Taylor et al. | 544/279 |
| 4,855,301 | 8/1989 | Atwal et al. | 544/316 |
| 4,882,334 | 11/1989 | Shih et al. | 544/279 |
| 4,902,796 | 2/1990 | Taylor et al. | 544/279 |
| 4,946,846 | 8/1990 | Nomura et al. | 544/280 |
| 5,134,145 | 7/1992 | Brouwer et al. | 514/274 |
| 5,149,810 | 9/1992 | Perrier et al. | 544/309 |
| 5,202,330 | 4/1993 | Atwal et al. | 544/316 |
| 5,250,531 | 10/1993 | Cooper | 514/256 |
| 5,292,740 | 3/1994 | Burri et al. | 514/256 |
| 5,500,424 * | 3/1996 | Nagamine et al. | 514/235.5 |
| 5,521,189 | 5/1996 | Boykin et al. | 514/256 |
| 5,541,186 | 7/1996 | Breu et al. | 514/256 |
| 5,594,141 | 1/1997 | Yuan et al. | 544/242 |
| 5,942,517 | 8/1999 | Nagarathnam et al. | 544/316 |

FOREIGN PATENT DOCUMENTS

| | | |
|---|---|---|
| 0162208 | 11/1985 | (EP) . |
| 0204317 | 12/1986 | (EP) . |
| 0234830 | 9/1987 | (EP) . |
| 0236902 | 9/1987 | (EP) . |
| 0237347 | 9/1987 | (EP) . |
| 0280227 | 8/1988 | (EP) . |
| 0400665 | 12/1990 | (EP) . |
| 0459666 | 12/1991 | (EP) . |
| 0622366 | 11/1994 | (EP) . |
| 0622369 | 11/1994 | (EP) . |
| 0627427 | 12/1994 | (EP) . |
| 2610625 | 8/1988 | (FR) . |
| 5659778 | 5/1981 | (JP) . |
| 9200741 | 1/1992 | (WO) . |
| 9214453 | 9/1992 | (WO) . |
| 9410989 | 5/1994 | (WO) . |
| 9422829 | 10/1994 | (WO) . |
| 97/17969 * | 5/1997 | (WO) . |
| 9742956 | 11/1997 | (WO) . |
| 9851311 | 11/1998 | (WO) . |
| 9907695 | 2/1999 | (WO) . |
| 9948530 | 9/1999 | (WO) . |

OTHER PUBLICATIONS

McGrath, J.C. et al., "Alpha–Adrenoceptors: A Critical Review," *Medicinal Research Reviews* (1989) 9(4): 407–533 (Exhibit 34).

Rovnyak, G.C. et al., "Dihydropyrimidine Calcium Channel Blockers. 4. Basic 3–Substituted–4–aryl–1, 4–dihydropyrimidine–5–carboxylic Acid Esters," *Journal of Medicinal Chemistry* (1992) 35(17): 3254–3263 (Exhibit 35).

Spiers, J.P. et al., UK–52,046 (A Novel $\alpha_1$–Adrenoceptor Antagonist) and the Role of $\alpha$–Adrenoceptor Stimulation and Blockade on Atrioventricular Conduction,: *Journal of Cardiovascular Pharmacology* (1990) 16(5): 824–830 (Exhibit 36).

Triggle, D.J., "Dihydropyrimidine Calcium Channel Blockers. 2.3–Substituted 4–Aryl–1, 4–dihydro–6–methyl–5–pyrimidine–Carboxylic Acid Esters as Potent Mimics of Dihydropyridines," *Chemtracts–Organic Chemistry* (Jan./Feb. 1991) 68–72 (Exhibit 37).

(List continued on next page.)

Primary Examiner—Mukund J. Shah
Assistant Examiner—Vankataraman Balasuhramanian
(74) Attorney, Agent, or Firm—John P. White; Cooper & Dunham LLP

(57) ABSTRACT

This invention is directed to dihydropyrimidine compounds which are selective antagonists for human $\alpha_{1A}$ receptors. This invention is also related to uses of these compounds for lowering intraocular pressure, inhibiting cholesterol synthesis, relaxing lower urinary tract tissue, the treatment of benign prostatic hyperplasia, impotency, cardiac arrhythmia and for the treatment of any disease where the antagonism of the $\alpha_{1A}$ receptor may be useful. The invention further provides a pharmaceutical composition comprising a therapeutically effective amount of the above-defined compounds and a pharmaceutically acceptable carrier.

19 Claims, No Drawings

OTHER PUBLICATIONS

Wetzel, J.M., et al., "Discovery of $\alpha_{1a}$-Adrenergic Receptor Antagonists Based on the L-Type $Ca^{2+}$ Channel Antagonist Niguldipine" *Journal of Medicinal Chemistry* (1995) 38(10): 1579–1581 (Exhibit 38).

Zhan, G.L. et al., "Bunazosin Reduces Intraocular Pressure By Increasing Uveoscleral Outflow In Rabbits," *Investigative Ophthalmology and Visual Science* (1993) 34(4): Abst. No. 1133–1149, p. 928 (Exhibit 39).

Atwal, K.S. et al., "Synthesis of Substituted 1,2,3,4–Tetrahydro–6–Methyl–2–Thioxo–5–Pyrimidinecarboxylic Acid Esters," *Heterocycles* (1987) 26(5): 1189–1192 (Exhibit 24).

Atwal, K.S. et al., "Substituted 1,4–Dihydropyrimidines. 3. Synthesis of Selectively Functionalized 2–Hetero–1,4–dihyropyrimidines," *Journal of Organic Chemistry* (1989) 54:5898–5907 (Exhibit 25).

Atwal, K.S. et al., "Dihydropyrimidine Calcium Channel Blockers: 2–Heterosubstituted 4–aryl–1,4–dihydro–6–methyl–5–pyrimidinecarboxylic Acid Esters as Potent Mimics of Dihydropyridines," *Journal of Medicinal Chemistry* (1990) 33(5): 1510–1515 (Exhibit 26).

Atwal, K.S. et al., "Dihydropyrimidine Calcium Channel Blockers. 2. 3–Substituted–4–aryl–1,4–dihydro–6–methyl–5–pyrimidinecarboxylic Acid Esters as Potent Mimics of Dihydropyridines," *Journal of Medicinal Chemistry* (1990), 33(9): 2629–2635 (Exhibit 27).

Atwal, K.S. et al., "Dihydropyrimidine Calcium Channel Blockers. 3. 3–Carbamoyl–4–aryl–1,2,3,4–tetrahydro–6–methyl–5–pyrimidenecarboxylic Acid Esters as Orally Effective Antihypertensive Agents," *Journal of Medicinal Chemistry* (1991) 34(2): 806–811 (Exhibit 28).

Boer, R., et al., "(+)–Niguldipine binds with very high affinity to $Ca^{2+}$ channels and to a subtype of $\alpha_1$–adrenoceptors," *European Journal of Pharmacology –Molecular Pharmacology Section* (1989) 172: 131–145 (Exhibit 29).

Cho, H. et al., "Dihydropyrimidines: Novel Calcium Antagonists with Potent and Long–Lasting Vasodilative and Antihypertensive Activity," *Journal of Medicinal Chemistry* (1989) 32: 2399–2406 (Exhibit 30).

D'Eletto, R.D. and Javitt, N.B., "Effect of Doxazosin on Cholesterol Synthesis In Cell Culture," *Journal of Cardiovascular Pharmacology* (1989) 13, Supp. 2: S1–S4 (Exhibit 31).

Khanina, E.L. et al., Alkylation of derivatives of 2–oxo–4–phenyl–6–methyl–1,2,3,4–tetrahydropyrimidine–5–carboxlic acid. *Chemical Abstracts* 89: 43319 (1978) (Exhibit 32).

Mamaev, V.P. and Dubovenko, Z.D., Pyrimidines. XXI. 5–Substituted 2–hydroxy–4,6–diphenylpyrimidines. *Chemical Abstracts* 73: 77187 (1970) (Exhibit 33).

Barrio, et al., "A Direct Method For The Preparation of 2–Hydroxyethoxymethyl Derivatives of Guanine, Adenine, and Cytosine" *Journal of Medicinal Chemistry* (1980) 23: 572–574.

Brown, et al., "Inhibitors of *Bacillus Subtilis* DNA Polymerase III 6–(Arylalkylamino)uracils and 6–Anilinouracil-sacils" *Journal of Medicinal Chemistry* (1977) 20(9): 1186–1189.

Forray, et al., "The $-_1$–Adrenergic Receptor That Mediates Smooth Muscle Contraction in Human Prostate Has the Pharmacological Properties of The Cloned Human $_{1c}$ Subtype" *Molecular Pharmacology* (1994) 45: 703–708.

\* cited by examiner

DIHYDROPYRIMIDINES AND USES THEREOF

This application claims the benefit of U.S. Provisional Application No. 60/017,582, filed May 16, 1996, the contents of which are hereby incorporated in its entirety by reference into the present application.

Throughout this application, various references are referred to within parentheses. Disclosures of these publications in their entireties are hereby incorporated by reference into this application to more fully describe the state of the art to which this invention pertains.

BACKGROUND OF THE INVENTION

The designation "$\alpha_{1A}$" is the appellation recently approved by the IUPHAR Nomenclature Committee for the previously designated "$\alpha_{1C}$" cloned subtype as outlined in the 1995 Receptor and Ion Channel Nomenclature Supplement (Watson and Girdlestone, 1995). The designation $\alpha_{1A}$ is used throughout this application and the supporting tables and figures to refer to this receptor subtype. At the same time, the receptor formerly designated $\alpha_{1A}$ was renamed $\alpha_{1D}$. The new nomenclature is used throughout this application. Stable cell lines expressing these receptors are described herein; however, these cell lines were deposited with the American Type Culture Collection (ATCC) under the old nomenclature (infra).

Benign Prostatic Hyperplasia (BPH), also called Benign Prostatic Hypertrophy, is a progressive condition which is characterized by a nodular enlargement of prostatic tissue resulting in obstruction of the urethra. This results in increased frequency of urination, nocturia, a poor urine stream and hesitancy or delay in starting the urine flow. Chronic consequences of BPH can include hypertrophy of bladder smooth muscle, a decompensated bladder and an increased incidence of urinary tract infection. The specific biochemical, histological and pharmacological properties of the prostate adenoma leading to the bladder outlet obstruction are not yet known. However, the development of BPH is considered to be an inescapable phenomenon for the aging male population. BPH is observed in approximately 70% of males over the age of 70. Currently, in the United States, the method of choice for treating BPH is surgery (Lepor, H., Urol. Clinics North Amer., 17, 651 (1990)). Over 400,000 prostatectomies are performed annually (data from 1986). A medicinal alternative to surgery is clearly very desirable. The limitations of surgery for treating BPH include the morbidity rate of an operative procedure in elderly men, persistence or recurrence of obstructive and irritative symptoms, as well as the significant cost of surgery.

α-Adrenergic receptors (McGrath, et. al. Med. Res. Rev., 9, 407–533, 1989) are specific neuroreceptor proteins located in the peripheral and central nervous systems on tissues and organs throughout the body. These receptors are important switches for controlling many physiological functions and, thus, represent important targets for drug development. In fact, many α-adrenergic drugs have been developed over the past 40 years. Examples include clonidine, phenoxybenzamine and prazosin (treatment of hypertension), naphazoline (nasal decongestant), and apraclonidine (treating glaucoma). α-Adrenergic drugs can be broken down into two distinct classes: agonists (clonidine and naphazoline are agonists), which mimic the receptor activation properties of the endogenous neurotransmitter norepinephrine, and antagonists (phenoxybenzamine and prazosin are antagonists), which act to block the effects of norepinephrine. Many of these drugs are effective but also produce unwanted side effects (for example, clonidine produces dry mouth and sedation in addition to its antihypertensive effects).

During the past 15 years a more precise understanding of α-adrenergic receptors and their drugs has evolved through increased scientific scrutiny. Prior to 1977, only one α-adrenergic receptor was known to exist. Between 1977 and 1988, it was accepted by the scientific community that at least two α-adrenergic receptors—$\alpha_1$ and $\alpha_2$—existed in the central and peripheral nervous systems. Since 1988, new techniques in molecular biology have led to the identification of at least six α-adrenergic receptors which exist throughout the central and peripheral nervous systems: $\alpha_{1A}$ (new nomenclature), $\alpha_{1B}$, $\alpha_{1D}$ (new nomenclature), $\alpha_{2A}$, $\alpha_{2B}$ and $\alpha_{2C}$ (Bylund, D. B., FASEB J., 6, 832 (1992)). In many cases, it is not known precisely which physiological responses in the body are controlled by each of these receptors. In addition, current α-adrenergic drugs are not selective for any particular α-adrenergic receptor. Many of these drugs produce untoward side effects which may be attributed to their poor α-adrenergic receptor selectivity.

Since the mid 1970's, nonselective α-antagonists have been prescribed to treat BPH. In 1976, M. Caine, et al. (Brit. J. Urol., 48, 255 (1976)), reported that the nonselective α-antagonist phenoxybenzamine was useful in relieving the symptoms of BPH. This drug may produce its effects by interacting with α-receptors located on the prostate. However, this drug also produces significant side effects such as dizziness and asthenia which severely limit its use in treating patients on a chronic basis. More recently, the α-adrenergic antagonists prazosin and terazosin have also been found to be useful for treating BPH. However, these drugs also produce untoward side effects. It has recently been discovered that the $\alpha_{1A}$ receptor is responsible for mediating the contraction of human prostate smooth muscle (Gluchowski, C. et. al., WO 94/10989, 1994; Forray, C. et. al., Mol. Pharmacol. 45, 703, 1994). This discovery indicates that the $\alpha_{1A}$ antagonists may be effective agents for the treatment of BPH with decreased side effects. Further studies have indicated that the $\alpha_{1A}$ receptor may also be present in other lower urinary tract tissues, such as urethral smooth muscle (Ford et al. Br. J. Pharmacol., 114, 24P, (1995)).

This invention is directed to dihydropyrimidine compounds which are selective antagonists for cloned human $\alpha_{1A}$ receptors. This invention is also related to uses of these compounds for lowering intraocular pressure (Zhan, et. al. Ophthalmol. Vis. Sci., 34 Abst. #1133, 928, 1993), inhibiting cholesterol synthesis (D'Eletto and Javitt, J. Cardiovascular Pharmacol., 13 (Suppl. 2) S1–S4, 1989), benign prostatic hyperplasia, impotency (Milne and Wyllie, EP 0 459 666 A2, 1991), sympathetically mediated pain (Campbell, WO 92/14453, 1992), cardiac arrhythmia (Spiers, et. al., J. Cardiovascular Pharmacol., 16, 824–830, 1990) and for the treatment of any disease where antagonism of the $\alpha_{1A}$ receptor may be useful.

SUMMARY OF THE INVENTION

This invention is directed to dihydropyrimidine compounds which are selective antagonists for human $\alpha_{1A}$ receptors. This invention is also related to uses of these compounds for lowering intraocular pressure, inhibiting cholesterol synthesis, relaxing lower urinary tract tissue, the treatment of benign prostatic hyperplasia, impotency, cardiac arrhythmia and for the treatment of any disease where antagonism of the $\alpha_{1A}$ receptor may be useful. The invention further provides a pharmaceutical composition comprising a therapeutically effective amount of the above-defined compounds and a pharmaceutically acceptable carrier.

DETAILED DESCRIPTION OF THE INVENTION

The present invention is directed to compounds having the structures:

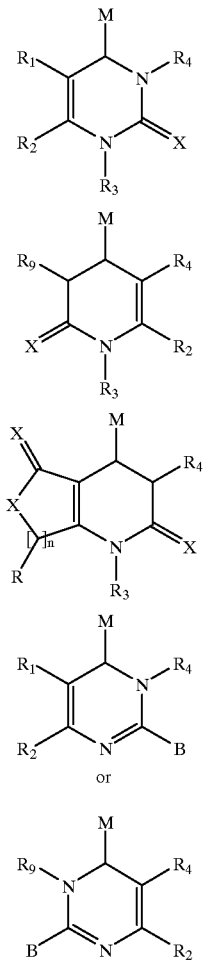

where M has the structure

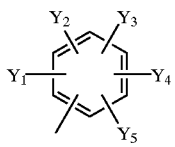

wherein each of $Y_1$, $Y_2$, $Y_3$, $Y_4$ and $Y_5$ independently may be —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —F, —Cl, —Br, or —I; —NO$_2$; —N(R$_3$)$_2$; —N$_3$; —CN; —OR$_3$; —OCOR$_3$; —COR$_3$; —CON(R$_3$)$_2$; or —CO$_2$R$_3$; or wherein two of $Y_1$, $Y_2$, $Y_3$, $Y_4$ and $Y_5$ are present on adjacent carbon atoms and together constitute a methylenedioxy group;

where R independently may be —H; —F; straight chained or branched $C_1$–$C_7$ alkyl, monofluoroalkyl or polyfluoroalkyl; straight chained or branched $C_2$–$C_7$ alkenyl or alkynyl; —N(R$_3$)$_2$; —NO$_2$; —CN; —CO$_2$R$_3$; —(CH$_2$)$_p$OR$_3$; or —OR$_3$;

where $R_1$ may be —H; —NO$_2$; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N(R$_3$)$_2$; —OR$_3$; —(CH$_2$)$_p$OR$_3$; —COR$_3$; —CO$_2$R$_3$; or —CON(R$_3$)$_2$, wherein any p independently is an integer from 1 to 7 inclusive;

where $R_2$ may be —H; straight chained or branched $C_1$–$C_7$ alkyl, hydroxyalkyl, alkoxyalkyl, aminoalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; $C_3$–$C_1$ cycloalkyl-$C_1$–$C_{10}$-alkyl, $C_3$–$C_{10}$ cycloalkyl-$C_1$–$C_{10}$-monofluoroalkyl or $C_3$–$C_{10}$ cycloalkyl-$C_1$–$C_{10}$-polyfluoroalkyl; —CN; —CH$_2$XR$_3$, —CH$_2$X(CH$_2$)$_p$NHR$_3$, —(CH$_2$)$_n$NHR$_3$, —CH$_2$X(CH$_2$)$_p$N(R$_3$)$_2$, —CH$_2$X(CH$_2$)$_p$N$_3$, or —CH$_2$X(CH$_2$)$_p$NHCXR$_7$; or —OR$_3$;

wherein any n independently is an integer from 0 to 5 inclusive and p is as defined above;

where each $R_3$ independently may be —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —(CH$_2$)$_p$OH; or —(CH$_2$)$_p$CO$_2$R$_8$;

where $R_4$ has the structure

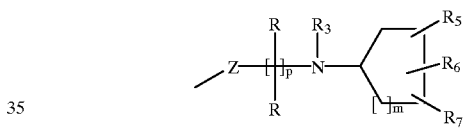

wherein Z may be $C_2$–$C_7$ alkenyl or alkynyl; CH$_2$; O; CO; CO$_2$; CONR$_3$CO; CONR$_3$; S; SO; SO$_2$; or NR$_3$; m is an integer from 0 to 3 inclusive;

$R_5$ and $R_6$ each independently may be —H; —F, —Cl, —Br, —I; —CO$_2$R$_3$; —COR$_3$; —CON(R$_3$)$_2$; —CN; —NO$_2$; —N(R$_3$)$_2$; —OR$_3$; straight chained or branched $C_1$–$C_7$ alkyl, $C_1$–$C_7$ monofluoroalkyl, $C_1$–$C_7$ polyfluoroalkyl, $C_2$–$C_7$ alkenyl, $C_2$–$C_7$ alkynyl, $C_3$–$C_7$ cycloalkyl, or $C_3$–$C_7$ cycloalkenyl, wherein the alkyl, monofluoroalkyl, polyfluoroalkyl, alkenyl, alkynyl, cycloalkyl or cycloalkenyl may be unsubstituted or substituted with —H, aryl or heteroaryl; aryl or heteroaryl wherein the aryl or heteroaryl may be unsubstituted or substituted with —H, —F, —Cl, —Br, —I, —NO$_2$, —CN, —N(R$_3$)$_2$, —OR$_3$, —COR$_3$, —CO$_2$R$_3$, or —CON(R$_3$)$_2$; straight chained or branched $C_1$–$C_7$ alkyl, monofluoroalkyl or polyfluoroalkyl, straight chained or branched $C_2$–$C_7$ alkenyl or alkynyl, $C_3$–$C_7$ cycloalkyl, monofluorocycloalkyl, polyfluorocycloalkyl, or cycloalkenyl;

$R_7$ may be —H; straight chained or branched $C_1$–$C_7$ alkyl, hydroxyalkyl, aminoalkyl, alkoxyalkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —CN; —CO$_2$R$_3$; —COR$_3$; —CON(R$_3$)$_2$; or —OR$_3$;

where $R_8$ is —H; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl;

where $R_9$ may be —H; —CN; straight chained or branched $C_1$–$C_7$ alkyl, monofluoroalkyl or polyfluoroalkyl; straight chained or branched $C_2$–$C_7$ alkenyl or alkynyl; $C_3$–$C_7$ cycloalkyl, monofluorocycloalkyl, polyfluorocycloalkyl or cycloalkenyl; —N($R_3$)$_2$; —O$R_3$; —(CH$_2$)$_p$O$R_3$; —CO$R_3$; —CO$_2$$R_3$; or —CON($R_3$)$_2$;

wherein X may be S; O; or N$R_3$; and wherein B may be —H; straight chained or branched $C_1$–$C_7$ alkyl, monofluoroalkyl, polyfluoroalkyl, alkoxy or thioalkyl; straight chained or branched $C_2$–$C_7$ alkenyl; —SCH$_2$C$_6$H$_4$O$R_3$; —(CH$_2$)$_n$C$_6$H$_5$; —CH$_2$X(CH$_2$)$_n$NH$R_3$; —(CH$_2$)$_n$NH$R_3$; or —O$R_3$;

or a pharmaceutically acceptable salt thereof.

In the present invention aryl includes benzyl, benzoyl, naphthyl, or phenyl and heteroaryl includes pyridyl, thienyl, furanyl, pyrazinyl, pyrrolyl, indolyl, imidazolyl, benzfurazanyl, benzo[b]furanyl, quinolinyl, benzimidazolyl or 2-keto-1-benzimidazolinyl.

The compounds of the present invention may be present as enantiomers, disteriomers, isomers or two or more of the compounds may be present to form a racemic mixture.

Furthermore, the compounds of the present invention are preferably at least 80% pure, more preferably 90% pure, and most preferably 95% pure.

The invention further provides for the (+) enantiomer of any of the compounds described herein which is a cis isomer or trans isomer. The invention also provides for the (−) enantiomer of any of the compounds described herein which is a cis isomer or trans isomer.

In one embodiment of the invention the compound is not (+)-6-(3,4-Difluorophenyl)-1-(N-[2-(4-cyano-4-phenyl-cyclohexylamino)ethyl]}carboxamido-5-methoxycarbonyl-4-methoxymethyl-2-oxo-1,2,3,6-tetrahydropyrimidine hydrochloride.

Ten-fold selectivity differences are a minimum, but one skilled in the art will appreciate that compounds can be found that collectively have almost infinitely variable selective profiles. Compounds collectively having all possible combinations of selectivities are intended within the scope of this invention, provided that each of these compounds has at least a ten-fold greater affinity for the $\alpha_{1A}$ receptor over the $\alpha_{1B}$ and/or $\alpha_{1D}$ receptors.

Preferred embodiments of the present invention include a compound selected from the group consisting of:

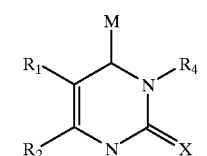

and

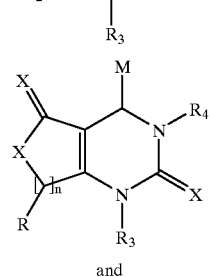

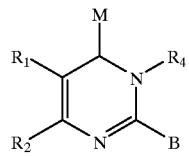

In one preferred embodiment for the compounds described herein $R_4$ is

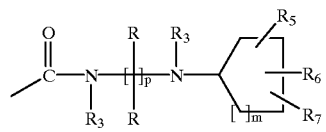

and p is 2, 3 or 4.

In one preferred embodiment for the compounds described herein $R_4$ is

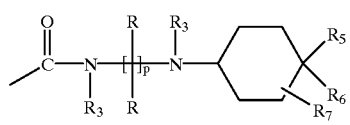

The invention also provides for compounds having the following structure:

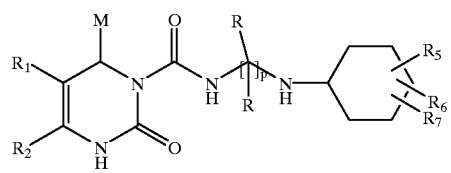

In one preferred embodiment of the present invention, M is polyfluorophenyl and $R_5$ and $R_6$ are independently substituted or unsubstituted phenyl or pyridyl.

In a further embodiment of the present invention, $R_1$ is —CO$_2$CH$_3$, —COCH$_3$, or —CONH$_2$, $R_2$ is CH$_2$OCH$_3$, methyl or ethyl; and $R_6$ is H, —CN, or CO$_2$CH$_3$.

The invention provides for the preferred embodiment having the following structures:

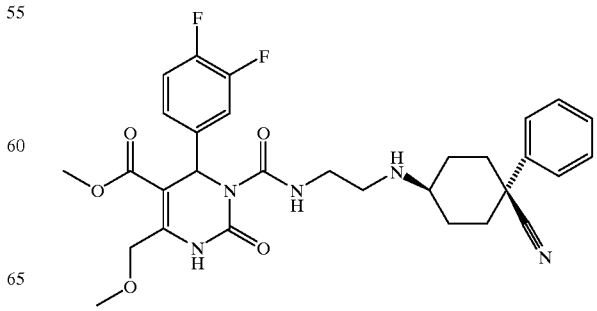

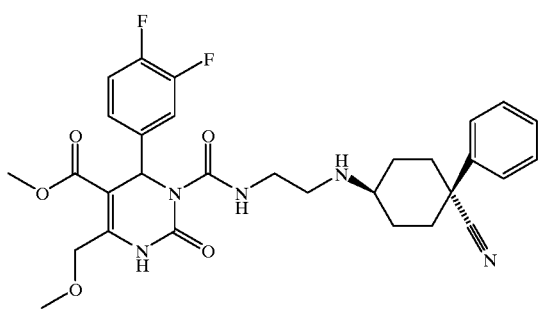

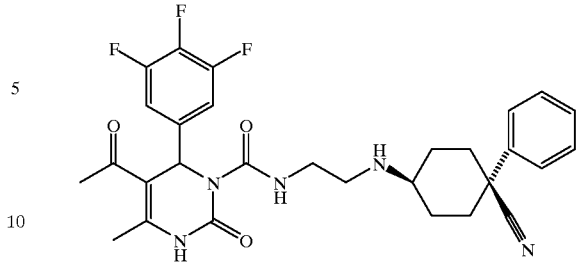

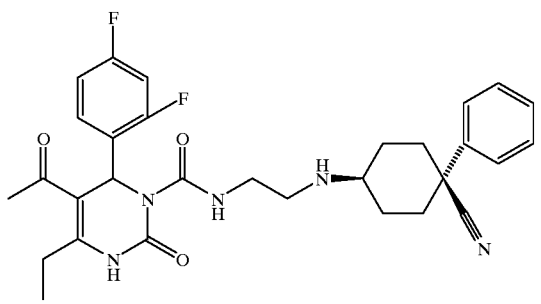

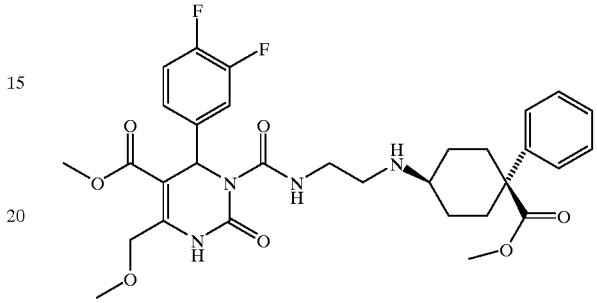

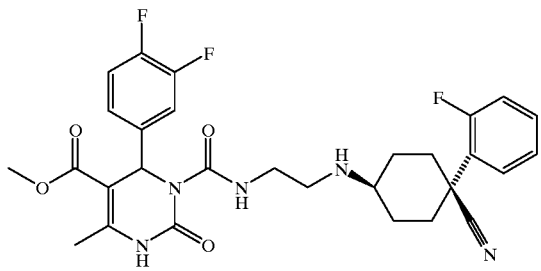

The invention also provides a pharmaceutical composition comprising a therapeutically effective amount of the compounds described above and a pharmaceutically acceptable carrier. In the subject invention a "therapeutically effective amount" is any amount of a compound which, when administered to a subject suffering from a disease against which the compounds are effective, causes reduction, remission, or regression of the disease. In one embodiment the therapeutically effective amount is an amount from about 0.01 mg per subject per day to about 500 mg per subject per day, preferably from about 0.1 mg per subject per day to about 60 mg per subject per day and most preferably from about 1 mg per subject per day to about 20 mg per subject per day. In the practice of this invention the "pharmaceutically acceptable carrier" is any physiological carrier known to those of ordinary skill in the art useful in formulating pharmaceutical compositions.

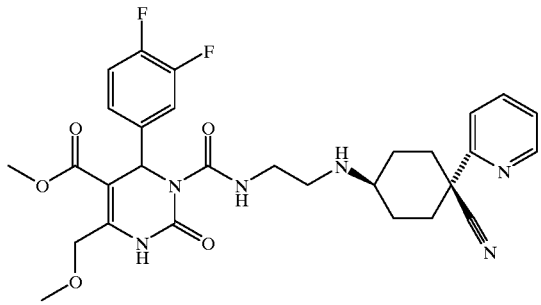

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream.

The invention provides a method of treating a subject suffering from benign prostatic hyperplasia which comprises administering to the subject any one of the compounds described herein effective to treat benign prostatic hyperplasia. The invention further provides that the compound additionally does not cause a fall in blood pressure at dosages effective to alleviate benign prostatic hyperplasia. In one preferred embodiment the compound effects treatment of benign prostatic hyperplasia by relaxing lower urinary tract tissue and in particular where the lower urinary tract tissue is prostatic smooth muscle.

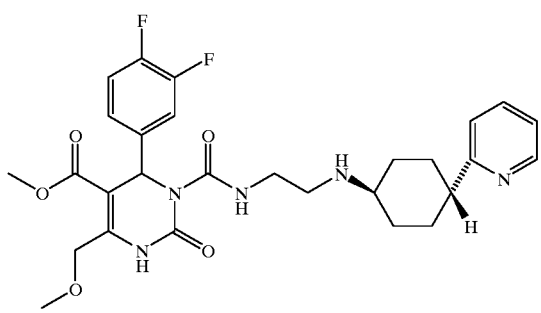

The invention further provides a method of treating a subject suffering from elevated intraocular pressure which comprises administering to the subject one of the compounds described herein effective to lower intraocular pressure.

The invention further provides a method of treating a subject suffering from a disorder associated with elevated blood cholesterol which comprises administering to the subject one of the compounds described herein effective to inhibit cholesterol synthesis.

The invention also provides a method of treating a disease which is susceptible to treatment by antagonism of the $\alpha_{1A}$ receptor which comprises administering to the subject one of the compounds described herein effective to treat the disease.

The invention further provides a method of treating a subject suffering from impotency which comprises administering to the subject one of the compounds described here in effective to treat impotency.

The invention further provides a method of treating a subject suffering from sympathetically mediated pain which comprises administering to the subject one of the compounds described herein effective to treat sympathetically mediated pain.

The invention provides a method of treating a subject suffering from cardiac arrhythmia which comprises administering to the subject one of the compounds described herein effective to treat cardiac arrhythmia.

This invention also provides a method of treating a subject suffering from benign prostatic hyperplasia which comprises administering to the subject an amount of any of the compounds described above in combination with a 5 alpha-reductase inhibitor effective to treat benign prostatic hyperplasia. Preferably, the 5-alpha reductase inhibitor is finasteride. The dosage administered to the subject is about 0.01 mg per subject per day to 50 mg per subject per day of finasteride in combination with an $\alpha_{1A}$ antagonist. A preferred dosage administered to the subject is about 0.2 mg per subject per day to 10 mg per subject per day of finasteride in combination with an $\alpha_{1A}$ antagonist. A more preferred dosage administered to the subject is about 1 mg per subject per day to 7 mg per subject per day of finasteride in combination with an $\alpha_{1A}$ antagonist. The most preferred dosage administered to the subject is about 5 mg per subject per day of finasteride in combination with an $\alpha_{1A}$ antagonist.

The invention also provides for a pharmaceutical composition comprising a therapeutically effective amount of a combination of any of the compounds described herein in combination with finasteride and a pharmaceutically acceptable carrier. In one embodiment the pharmaceutical composition is a therapeutically effective amount of a combination comprising an amount from about 0.01 mg per subject per day to about 500 mg per subject per day of any one of the compounds described herein and an amount of finasteride of about 5 mg per subject per day. A more preferred embodiment of the pharmaceutical composition is a therapeutically effective amount of a combination comprising an amount from about 0.1 mg per subject per day to about 60 mg per subject per day of any one of the compounds described herein and an amount of the finasteride of about 5 mg per subject per day. The most preferred embodiment of the pharmaceutical composition is a therapeutically effective amount of a combination comprising from about 1 mg per subject per day to about 20 mg per subject per day of any one of the compounds described herein and an amount of the finasteride of about 5 mg per subject per day.

The invention further provides a method of relaxing lower urinary tract tissue which comprises contacting the lower urinary tract tissue with an amount of one of the compounds described herein effective to relax lower urinary tract tissue. In one embodiment the lower urinary tract tissue is prostatic smooth muscle. In one preferred embodiment the compound additionally does not cause a fall in blood pressure when it is effective to relax lower urinary tract tissue.

The invention provides a method of relaxing lower urinary tract tissue in a subject which comprises administering to the subject an amount of one of the compounds described herein effective to relax lower urinary tract tissue. In one preferred embodiment the compound does not cause a fall in blood pressure and the lower urinary tract tissue is prostatic smooth muscle.

The invention further provides for a method of inhibiting contraction of prostatic tissue, which comprises administering to the subject an amount of any of the compounds described herein effective to inhibit contraction of prostatic tissue. In one preferred embodiment the prostatic tissue is prostatic smooth muscle and the compound additionally does not cause a fall in blood pressure.

The invention provides for the use of the compounds described herein for the preparation of a pharmaceutical composition for lowering intraocular pressure, inhibiting cholesterol synthesis, and the treatment of: benign prostatic hyperplasia, impotency, cardiac arrhythmia and any disease where antagonism of the $\alpha_{1A}$ receptor may be useful. The invention provides for the use of the compounds described herein for the preparation of a pharmaceutical composition for relaxing lower urinary tract tissue and in particular prostatic smooth muscle. The invention further provides for the use of any of compounds described herein for the preparation of a pharmaceutical composition, where the compound additionally does not cause a fall in blood pressure at dosages effective to lower intraocular pressure, to inhibit cholesterol synthesis, and for the treatment of: benign prostatic hyperplasia, impotency, cardiac arrhythmia and any disease where antagonism of the $\alpha_{1A}$ receptor may be useful.

The invention provides for the use of the compounds described herein in the preparation of a medicament for lowering intraocular pressure, inhibiting cholesterol synthesis, and for the treatment of: benign prostatic hyperplasia, impotency, cardiac arrhythmia and any disease where antagonism of the $\alpha_{1A}$ receptor may be useful. The invention provides for the use of the compounds described herein in the preparation of a medicament for relaxing lower urinary tract tissue and in particular prostatic smooth muscle. The invention further provides for the use of any of compounds described herein in the preparation of a medicament, where the compound additionally does not cause a fall in blood pressure at dosages effective to lower intraocular pressure, to inhibit cholesterol synthesis, and for the treatment of: benign prostatic hyperplasia, impotency, cardiac arrhythmia and any disease where antagonism of the $\alpha_{1A}$ receptor may be useful.

The invention provides for a drug which is useful for lowering intraocular pressure, inhibiting cholesterol synthesis, and the treatment of: benign prostatic hyperplasia, impotency, cardiac arrhythmia and any disease where antagonism of the $\alpha_{1A}$ receptor may be useful, the effective ingredient of the said drug being any of the compounds described herein. The invention further provides the drug described herein additionally does not cause a fall in blood pressure at dosages effective to lower intraocular pressure, to inhibit cholesterol synthesis, and for the treatment of: benign prostatic hyperplasia, impotency, cardiac arrhythmia and any disease where antagonism of the $\alpha_{1A}$ receptor may be useful.

The invention provides for a drug which is useful for relaxing lower urinary tract tissue and in particular prostatic smooth muscle, the effective ingredient of the drug being any of the compounds described herein. The invention further provides the drug which is useful for relaxing lower urinary tract tissue additionally does not cause a fall in blood pressure at dosages effective to relax lower urinary tract tissue.

The invention also provides for the (−) and (+) enantiomers of all compounds of the subject application described herein. Included in this invention are pharmaceutically acceptable salts and complexes of all of the compounds described herein. The salts include but are not limited to the following acids and bases. The following inorganic acids; hydrochloric acid, hydrofluoric acid, hydrobromic acid, hydroiodic acid, sulfuric acid and boric acid. The organic acids; acetic acid, trifluoroacetic acid, formic acid, oxalic acid, malonic acid, succinic acid, fumaric acid, tartaric acid, maleic acid, citric acid, methanesulfonic acid, trifluoromethanesulfonic acid, benzoic acid, glycolic acid, lactic acid and mandelic acid. The following inorganic bases; ammonia, hydroxyethylamine and hydrazine. The following organic bases; methylamine, ethylamine, propylamine, dimethylamine, diethylamine, trimethylamine, triethylamine, ethylenediamine, hydroxyethylamine, morpholine, piperazine and guanidine. This invention further provides for the hydrates and polymorphs of all of the compounds described herein.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the compound may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The compounds may be prepared as a sterile solid composition which may be dissolved or suspended at the time of administration using sterile water, saline, or other appropriate sterile injectable medium. Carriers are intended to include necessary and inert binders, suspending agents, lubricants, flavorants, sweeteners, preservatives, dyes, and coatings.

The compound can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The compound can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration.

One skilled in the art will readily appreciate that appropriate biological assays will be used to determine the therapeutic potential of the claimed compounds for treating the above noted disorders.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

For Examples 1–17 Scheme 1 illustrates the general synthetic scheme for the preparation of the compounds of the present invention. Specific references to synthetic steps from Schemes 2–8 are included in the Examples below where appropriate. All NMRs were obtained using a 300 MHz GE QEPLUS NMR machine.

EXAMPLE 1 cis-6-(3,4-Difluorophenyl)-1-{N-[2-(4-cyano-4-phenylcyclohexylamino)ethyl]}carboxamido-5-methoxycarbonyl-4-methyl-2-oxo-1,2,3,6-tetrahydropyrimidine hydrochloride
Part 1
a) General procedure for 2-[4-Cyano-4-aryl-cyclohexylamino]ethylamine (Scheme 2; Part 1)

A mixture of 4-cyano-4-aryl-cyclohexanone (48.7 mmol) and ethylenediamine (8.78 g, 146 mmol) and p-toluenesulfonic acid (92 mg) in benzene (200 mL) was refluxed for 4 h in Dean-Stark trap to remove the water that formed. Solvent was evaporated and the residue was redissolved in methanol (60 mL) and cooled to 0° C. Sodium borohydride (6.4 5 g) was added in portions and the mixture was stirred at room temperature for 3 h. Solvent was evaporated, the residue was dissolved in dichloromethane (300 mL), washed with brine (3×500 mL), dried (potassium carbonate), and the solvent evaporated to leave the product as a pale yellow viscous oil (90–95%). The product was found to contain the cis/trans isomers in the ratio of about 9:1. Careful chromatography of this mixture with chloroform/methanol/2M ammonia in methanol (100/10/5 to 100/20/10) yielded several some earlier fractions enriched in the trans isomer with respect to the amino and cyano groups. Later fractions eluted contained almost pure cis isomer relative to the amino and cyano groups.

Part 2 b) Methyl 2-{(3,4-difluorophenyl)methylene}-3-oxobutyrate (Scheme 2; Step C)

A mixture of 3,4-difluorobenzaldehyde (14.2 g, 0.1 mol), methyl acetoacetate (12.2 g, 0.105 mol), piperidine (0.430 g, 5 mmol), and acetic acid (0.30 g, 5 mmol) in benzene (150 mL) was stirred and refluxed with a Dean-Stark trap for 8 hours. Benzene was evaporated, the residue was dissolved in ethyl acetate (200 mL) and washed with brine (50 mL), saturated potassium bisulfate solution (50 mL), and saturated sodium bicarbonate solution in sequence. The ethyl acetate solution was dried (magnesium sulfate), solvent removed under reduced pressure and the residue was purified by column chromatography (SiO2, EtOAc/hexane, 10%–15%). The product, methyl 2-{(3,4-difluorophenyl)methylene}-3-oxobutyrate, was obtained as a yellow oil (0.98 g, 98.3%) and was used in the next step without any further characterization.

c) 6-(3,4-Difluorophenyl)-1,6-dihydro-2-methoxy-5-methoxycarbonyl-4-methylpyrimidine (Scheme 2; Step D)

A mixture of methyl 2-{(3,4-difluorophenyl) methylene}-3-oxobutyrate (8.8 .g, 36.6 mmol), O-methylisourea hydrogen sulfate (9.4 g, 55 mmol), and $NaHCO_3$ (12.3 g, 0.146 mol) in DMF (30 mL) was stirred and heated at 70° C. for 16 hours. The mixture was cooled, diluted with EtOAc (300 mL) and washed with water (5×300 mL), brine (300 mL), and dried ($MgSO_4$). Solvent was evaporated and the crude product was purified by flash column chromatography on silica gel using 10% through 20% EtOAc in hexane as the gradient eluent, to leave the product as an oil (3.82 g, 30.2%)

d) 6-(3,4-Difluorophenyl)-1,6-dihydro-2-methoxy-5-methoxycarbonyl-4-methyl-1-[(4-nitrophenyloxy)carbonyl]pyrimidine (Scheme 2; E)

To a solution of 6-(3,4-difluorophenyl)-1,6-dihydro-2-methoxy-5-methoxycarbonyl-4-methylpyrimidine (2.82 g, 9.52 mmol) and 4-dimethylaminopyridine (1.16 g, 9.52 mmol) in $CH_2Cl_2$ (50 mL),at 0–5° C., 4-nitrophenyl chloroformate (1.82 g, 9.04 mmol) was added and the mixture was allowed to warm to room temperature. After 12 hours solvent was evaporated and the residue was purified by flash column chromatography (SiO2, EtOAc/hexane, 10%–15%) to obtain the product as white crystals (3.72, 84.7%); m.p. 172–174° C.

e) 6-(3,4-Difluorophenyl)-1,2,3,6-tetrahydro-2-oxo-5-methoxycarbonyl-4-methyl-1-(4-nitrophenoxy)carbonylpyrimidine (Scheme 2; Step F)

To a well stirred solution of 6-(3,4-difluorophenyl)-1,6-dihydro-2-methoxy-5-methoxycarbonyl-4-methyl-1-(4-nitrophenoxy)carbonylpyrimidine (10 g) in THF (200 mL) at room temperature was added aqueous 6 N hydrochloric acid (10 mL). The stirring was continued for 3 h. Solvent was evaporated and the residue was dried under vacuum to obtain the product as a white powder (9.7 g, 100%); m.p. 185–186° C.

Part 3 f) cis-6-(3,4-Difluorophenyl)-1-{N-[2-(4-cyano-4-phenyl-cyclohexylamino)ethyl]}carboxamido-5-methoxycarbonyl-4-methyl-2-oxo-1,2,3,6-tetrahydropyrimidine hydrochloride (Scheme 2; Step G)

A solution of 5-methoxycarbonyl-4-methyl-1,2,3,6-tetrahydro-2-oxo-6-(3,4-difluorophenyl)-1-[(4-nitrophenyloxy)carbonyl]pyrimidine (500 mg, 1.15 mmol) and cis-2-[4-cyano-4-phenyl-cyclohexylamino]ethylamine (351 mg, 1.5 mmol) in dichloromethane (50 mL) was stirred at room temperature for 12 hours. The solution was washed with ice-cold 0.5 N NaOH (2×10 mL) and dried over sodium sulfate. Solvent was evaporated at reduced pressure and the residue was purified by flash chromatography on silica gel (dichloromethane:MeOH:2M ammonia in MeOH, 90:8:4) to give 0.55 g (87%) as a white powder. The HCl salt was prepared by treatment of a solution of the free base in ether with 1 N HCl in ether. M.P. 172–174° C.; Anal. Calcd. for $C_{29}H_{31}N_5O_4F_2Cl.1.3H_2O$:C, 56.96; H, 5.70; N, 11.45. Found: C, 57.10; H, 5.69; N, 11.12.

EXAMPLE 2 cis-6-(3,4,5-Trifluorophenyl)-1-{N-[2-(4-cyano-4-phenyl-cyclohexylamino)ethyl]}-carboxamido-5-acetyl-4-methoxymethyl-2-oxo-1,2,3,6-tetrahydropyrimidine hydrochloride a) 3-{(3,4,5-Trifluorophenyl)methylene}-2,4-pentanedione (Scheme 2; Step C)

A mixture of 3,4,5-trifluorobenzaldehyde (4.2 g, 26.2 mmol), 2,4-pentanedione (2.62 g, 26.2 mmol), piperidine (0.430 g, 5 mmol) in benzene (150 mL) was stirred and refluxed with a Dean-Stark trap for 8 hours. Benzene was evaporated and the yellow oily residue, 2-{(3,4,5-trifluorophenyl)methylene}-2,4-pentanedione, was used in the next step without any further purification.

b) 6-(3,4,5-Trifluorophenyl)-1,6-dihydro-2-methoxy-5-acetyl-4-methylpyrimidine (Scheme 2; Step D)

A mixture of 2-{(3,4,5-trifluorophenyl)methylene}-2,4-pentanedione (26.2 mmol), O-methylisourea hydrogen sulfate (3.22 g, 39.3 mmol), and $NaHCO_3$ (6.6 g, 78.6 mmol) in EtOH (400 mL) was stirred and heated at 95–100 ° C. for 6 hours. The mixture was filtered and the solid residue was washed with ethanol (100 mL). Solvent was evaporated from the combined filtrate and the crude product was purified by flash column chromatography on silica gel using 10% through 25% EtOAc in hexane as the gradient eluent, to leave the product as an oil (2.80 g, 36%).

c) 6-(3,4,5-Trifluorophenyl)-1,6-dihydro-2-methoxy-5-acetyl-4-methyl-1-[(4-nitrophenyloxy)carbonyl]pyrimidine (Scheme 2; Step E)

To a solution of 6-(3,4,5-trifluorophenyl)-1,6-dihydro-2-methoxy-5-acetyl-4-methylpyrimidine (2.8 g, 9.38 mmol) and pyridine (10 mL) in $CH_2Cl_2$ (200 mL) at 0–5° C. was added 4-nitrophenyl chloroformate (1.886 g, 9.38 mmol) and the mixture was allowed to warm to room temperature. After 12 hours solvent was evaporated and the residue was purified by flash column chromatography (SiO2, dichloromethane/EtOAc, 10%–15%) to obtain the product as a white powder (4.0 g, 92%).

d) 6-(3,4,5-Trifluorophenyl)-1,2,3,6-tetrahydro-2-oxo-5-acetyl-4-methyl-1-[(4-nitrophenyloxy)carbonyl]pyrimidine (Scheme 2; Step F)

To a well-stirred solution of 6-(3,4,5-trifluorophenyl)-1,6-dihydro-2-methoxy-5-acetyl-4-methyl-1-[(4-nitrophenyloxy)carbonyl]pyrimidine (4.0 g, 8.63 mmol) in THF (100 mL) at 0–5° C., 6 N aqueous HCl (4 mL) was added and the mixture was allowed to warm to room temperature. After 2 h, solvent was evaporated and the product dried under vacuum. The title compound was obtained as a pure single component and used un the next step without further purification (3.88 g, 100%).

e) cis-6-(3,4,5-Trifluorophenyl)-1-{N-[2-(4-cyano-4-phenyl-cyclohexylamino)ethyl]}-carboxamido-5-acetyl-4-methoxymethyl-2-oxo-1,2,3,6-tetrahydropyrimidine hydrochloride (Scheme 2; Step G)

A mixture of 6-(3,4,5-trifluorophenyl)-1,2,3,6-tetrahydro-2-oxo-5-acetyl-4-methyl-1-[(4-nitrophenyloxy) carbonyl] pyrimidine (44.9 mg, 0.1 mmol) and cis-2-(4-cyano-4-phenyl-cyclohexylamino)ethylamine (23.4 mg, 0.23 mmol) in THF (10 mL) was stirred at room temperature for 10 h and the solvent evaporated. The residue was redissolved in dichloromethane (10 mL), washed with ice-cold 0.5 N NaOH (2×5 mL), dried and solvent evaporated. The residue was purified by preparative thin layer chromatography on silica gel using chloroform-methanol-2M ammonia in methanol (100/2/1) as the eluent to afford the product as a white powder (53 mg, 88%). The HCl salt was prepared by treatment with 1 N HCl in ether to give the product as a white powder. Anal. Calcd. for $C_{30}H_{32}N_5O_3ClF_3 \cdot 0.5CH_2Cl_2$: C, 56.66; H, 5.30; N, 10.83. Found: C, 56.51; H, 5.12; N, 11.09.

EXAMPLE 3
(+)-cis-5-Carboxamido-6-(2,4-difluorophenyl)-1-{N-[2-(4-cyano-4-phenyl-cyclohexylamino)ethyl]}carboxamido-4-ethyl-2-oxo-1,2,3,6-tetrahydropyrimidine hydrochloride a) Benzyl 2-[(2,4-difluorophenyl)methylene]-3-oxopentanoate (Scheme 2; Step C)

A solution of benzyl propionylacetate (157 g, 0.758 mol), 2,4-difluorobenzaldehyde (107.65 g, 0.758 mol), and piperidinium acetate (5.49 g, 38 mmol) in benzene (1 L) were stirred at room temperature for 96 h. The mixture was washed with water (2×100 mL), dried (magnesium sulfate) and the solvent evaporated under reduced pressure to yield the product as a pale yellow syrup (251.2 g) which was used in the next step without further purification.

b) 5-(Benzyloxycarbonyl)-1,6-dihydro-2-methoxy-4-ethyl-6-(2,4-difluorophenyl)pyrimidine (Scheme 2; Step D)

A suspension of benzyl 2-[(2,4-difluorophenyl)methylene]-3-oxopentanoate (80.0 g, 0.241 mol), O-methylisourea hemisulfate (63.8 g, 0.362 mol, 1.5 eq.), NaHCO$_3$ (60.48 g, 0.72 mol) in ethanol (800 mL) was stirred at 60–70° C. for 20 h. After cooling to room temperature, the mixture was filtered, and the solid was washed with ethanol (200 mL). The solvent was evaporated from the combined filtrates and the residue was purified by column chromatography (SiO$_2$, EtOAc/Hexane, 10%–30%) to yield 5-(benzyloxycarbonyl)-1,6-dihydro-2-methoxy-4-ethyl-6-(2,4-difluorophenyl) pyrimidine as a pale yellow oil (39 g, 42%). $^1$H-NMR analysis showed the product to be a mixture of amine/imine tautomers, which was used as is in the next step.

c) 5-(Benzyloxycarbonyl)-4-ethyl-1,6-dihydro-2-methoxy-6-(2,4-difluorophenyl)-1-[(4-nitrophenyloxy) carbonyl] pyrimidine (Scheme 2; Step F)

To a well stirred solution of 5-(benzyloxycarbonyl)-1,6-dihydro-2-methoxy-4-ethyl-6-(2,4-difluorophenyl) pyrimidine (22.5 g, 59.3 mmol) and 4-(N,N-dimethylamino) pyridine (9.3 g, 75.8 mmol) in CH$_2$Cl$_2$ (200 mL) was added powdered 4-nitrophenyl chloroformate (15.3 g, 75.8 mmol) at 0° C. The reaction mixture was stirred for 12 h at room temperature and then water (50 mL) was added. The pH of the aqueous layer was adjusted to 10–11 by the addition of 6 N sodium hydroxide. The dichloromethane layer was separated and dried (Na$_2$SO$_4$). Solvent was evaporated in vacuo and the residue was purified by column chromatography (SiO$_2$, dichloromethane/hexane, 20%–50%) to yield the product as a viscous oil (32.0 g, 98%).

d) 5-(Benzyloxycarbonyl)-4-ethyl-1,6-dihydro-1-{N-[2-phenyl)ethyl]}carboxamido-2-methoxy-6-(2,4-difluorophenyl)pyrimidine (Scheme 3; Steps C-1 & C-2)

To a stirred solution of 5-(benzyloxycarbonyl)-4-ethyl-1,6-dihydro-2-methoxy-6-(2,4-difluorophenyl)-1-[(4-nitrophenyloxy)carbonyl]pyrimidine (32 g, 58.17 mmol) in dichloromethane (200 mL) was added R-(+)-α-methylbenzylamine (9.16, 75.6 mmol) at room temperature. The mixture was stirred for 12 h and then was diluted with more dichloromethane (200 mL) and washed with 0.5 N NaOH solution (2×60 mL). The organic layer was dried over Na$_2$SO$_{41}$ filtered and solvent was evaporated. The resulting mixture of diastereomers was separated by column chromatography (SiO$_2$, 3% EtOAc in toluene). The first major product to elute was (+)-5-(benzyloxycarbonyl)-4-ethyl-1,6-dihydro-1-{N-[2-phenyl)ethyl]}carboxamido-2-methoxy-6-(2,4-difluorophenyl)pyrimidine (12.15 g, 38%). [α]$_D$=+214 (c=1.5 g in 100 mL CHCl$_3$).

e) (+)-5-(Benzyloxycarbonyl)-1,6-dihydro-2-methoxy-4-ethyl-6-(2,4-difluorophenyl)pyrimidine (Scheme 3; Step C-3)

To a stirred solution of (+) -5 (benzyloxycarbonyl)-4-ethyl-1,6-dihydro-1-{N-[2-phenyl)ethyl]}carboxamido-2-methoxy-6-(2,4-difluorophenyl)pyrimidine (11.15 g, 20.41 mmol) in toluene (250 mL) was added 1,8-diazabicyclo[5,4,0]-undec-7-ene (4.04 g, 26.53 mmol) and the mixture was stirred at room temperature for 14 h. The solvent was evaporated and the residue was purified by flash column chromatography on silica gel with 3:1 EtOAc/hexane as eluent to give (+)-5-(benzyloxycarbonyl)- 1,6-dihydro-2-methoxy-4-ethyl-6-(2,4-difluorophenyl)pyrimidine as a viscous oil (6.15 g, 78%).

f) (+)-5-(Benzyloxycarbonyl)-4-ethyl-1,6-dihydro-2-methoxy-6-(2,4-difluorophenyl)-1-[(4-nitrophenyl-oxy)carbonyl]pyrimidine (Scheme 2; Step E)

To a well stirred solution of (+)-5-(benzyloxycarbonyl)-1,6-dihydro-2-methoxy-4-ethyl-6-(2,4-difluorophenyl) pyrimidine (4.1 g, 10.62 mmol) and 4-(N,N-dimethylamino) pyridine (1.69 g, 13.80 mmol) in CH$_2$Cl$_2$ (200 mL) was added solid 4-nitrophenyl chloroformate (2.78 g, 13.80 mmol) at room temperature. The reaction mixture was stirred for 12 h and washed with 0.5 N NaOH solution (2×50 mL). The organic layer was separated and dried (Na$_2$SO$_4$). The solvent was evaporated and the residue was purified by column chromatography on silica gel using dichloromethane/hexane (20%–50%) as the eluent to give (+)-5-(benzyloxycarbonyl)-4-ethyl-1,6-dihydro-2-methoxy-6-(2,4-difluorophenyl)-1-[(4-nitrophenyloxy)carbonyl] pyrimidine (5.37 g, 92%) as a viscous oil.

g) (+)-5-Benzyloxycarbonyl-4-ethyl-1,2,3,6-tetrahydro-2-oxo-6-(2,4-difluorophenyl)-1-[(4-nitrophenyloxy) carbonyl] pyrimidine (Scheme 4; Step A)

To a solution of (+)-6-(2,4-difluorophenyl)-1,6-dihydro-2-methoxy-5-benzyloxycarbonyl-4-ethyl-1-(4-nitrophenoxy)-carbonylpyrimidine (6.50 g, 11.81 mmol) in dichloromethane (150 mL) at room temperature was added 1 N HCl in ether (50 mL) and the mixture was stirred at room temperature for 12 hours. Solvent was evaporated at reduced pressure and the residue was dried to give 6.31 g (100%) of the product as a white powder.

h) (+)-5-(Benzyloxycarbonyl)-6-(2,4-difluorophenyl)-4-ethyl-2-oxo-1,2,3,6-tetrahydro-1-{N-[2-(4-cyano-4-phenyl-cyclohexylamino)ethyl]}carboxamidopyrimidine (Scheme 4; Step B-1)

A mixture of (+)-5-benzyloxycarbonyl-4-ethyl-1,2,3,6-tetrahydro-2-oxo-6-(2,4-difluorophenyl)-1-[(4-nitrophenyloxy)carbonyl]pyrimidine (537 mg, 1 mmol) and cis-2-(4-cyano-4-phenyl-cyclohexylamino)ethylamine (281 mg, 1.2 mmol) in THF (20 mL) was stirred at room temperature for 10 h and the solvent evaporated. It was redissolved in dichloromethane (10 mL), washed with ice-cold 0.5 N NaOH (2×5 mL), dried and solvent evaporated. The residue was purified by preparative thin layer chromatography on silica gel using chloroform-methanol-2M ammonia in methanol (100/2/1) as the eluent to afford the product as a white powder (603 mg, 94%).

i) (+)-6-(2,4-Difluorophenyl)-4-ethyl-2-oxo-1,2,3,6-tetrahydro-1-{N-[2-(4-cyano-4-phenyl-cyclohexylamino)ethyl]}carboxamidopyrimidine-5-carboxylic acid (Scheme 4; Step B-2)

To a suspension of 10% Pd—C (100 mg) in MeOH (40 mL) and $H_2O$ (8 mL) was added a solution of (+)-5-(benzyloxycarbonyl)-6-(2,4-difluorophenyl)-4-ethyl-2-oxo-1,2,3,6-tetrahydro-1-{N-[2-(4-cyano-4-phenyl-cyclohexylamino)-ethyl]}carboxamidopyrimidine (320 mg, 0.5 mmol) in methanol (10 mL) and the mixture was hydrogenated at 80 psi for 6 h. The black suspension was filtered through a pad of celite and washed thoroughly with MeOH (2.0 L) and methanol/chloroform (1:2, 200 mL). Solvent was evaporated from the combined filtrate to yield the product (+)-cis-6-(2,4-difluorophenyl)-4-ethyl-2-oxo-1,2,3,6-tetrahydro-1-{N-[2-(4-cyano-4-phenyl-cyclohexylamino)-ethyl]}carboxamidopyrimidine-5-carboxylic acid as a white solid (276 g, 98%). The product was used in the next step without further purification.

j)(+)-cis-5-Carboxamido-6-(2,4-difluorophenyl)-1-{N-[2-(4-cyano-4-phenyl-cyclohexylamino)ethyl]}carboxamido-4-ethyl-2-oxo-1,2,3,6-tetrahydropyrimidine hydrochloride (Scheme 4; Step B-3)

A mixture of (+)-cis-6-(2,4-difluorophenyl)-4-ethyl-2-oxo-1,2,3,6-tetrahydro-1-{N-[2-(4-cyano-4-phenyl-cyclohexylamino)ethyl]}carboxamidopyrimidine-5-carboxylic acid (141 mg, 0.25 mmol), 1-(3-dimethylaminopropyl)-3-ethylcarbodiimide hydrochloride (71.3 mg, 0.372 mmol), and 4-(N,N-dimethylamino) pyridine (45.4 mg, 0.372 mmol) in anhydrous dichloromethane (30 mL) was stirred at room temperature for 2 h. 40% Aqueous ammonia (4090, 0.5 mL) was added to this mixture and the stirring was continued for 12 h. The mixture was diluted with 20 mL of dichloromethane and washed with saturated aqueous ammonium chloride solution (3×10 mL). Solvent was evaporated from the dried (sodium sulfate) dichloromethane solution and the residue was purified by column chromatography on silica gel using chloroform-methanol-2M ammonia in methanol (100/2/1) as the eluent, to obtain the desired product as a white powder (120 mg, 88%); $[\alpha]_D$=+107 (c=1.38 g, dichloromethane). The HCl salt was prepared by treatment of a solution of the free base in ether with 1 N HCl in ether. M.p. 225–228° C.; Anal. Calcd. for $C_{29}H_{33}N_6O_3F_2Cl.0.38H_2O.0.19CH_2Cl_2$: C, 57.47; H, 5.64; N, 13.75. Found: C, 57.80; H, 5.56; N, 13.37.

EXAMPLE 4

(+)-cis-6-(3,4-Difluorophenyl)-1-{N-[2-(4-cyano-4-phenyl-cyclohexylamino)ethyl]}carboxamido-5-methoxycarbonyl-4-methoxymethyl-2-oxo-1,2,3,6-tetrahydropyrimidine hydrochloride
Part 2 a) Methyl 2-[(3,4-difluorophenyl)methylene]-3-oxo-4-methoxybutyrate (Scheme 2; C)

To a solution of methyl 4-methoxyacetoacetate (84.32 g, 0.577 mol), 3,4-difluorobenzaldehyde (82 g, 0.577 mmol), and piperidinium acetate (5.86 g, 0.068 mol) in benzene (1.5 L) were added molecular sieves (400 g) and the mixture was stirred at room temperature for 48 h. The molecular sieves were removed by filtration and the solvent was evaporated from the filtrate under reduced pressure. The residue was purified by column chromatography on silica gel using chloroform/ethyl acetate (100:3) to get the product as an oil (67 g, 47%). This product was a mixture of cis and trans isomers.

b) 5-Methoxycarbonyl-1,6-dihydro-2-methoxy-4-methoxymethyl-6-(3,4-difluorophenyl)pyrimidine (Scheme 2; Step D)

A suspension of methyl 2-[(3,4-difluorophenyl)methylene]-3-oxo-4-methoxybutyrate (7.50 g, 27.75 mmol), O-methylisourea hemisulfate (7.17 g, 41.63 mmol, 1.5 eq.), and sodium bicarbonate (6.99 g, 83.25 mmol, 3 eq.) in ethanol (400 mL) was stirred at 50–55° C. for 6 h. The solvent was evaporated from the combined filtrates and the residue was purified by column chromatography ($SiO_2$, EtOAc/hexane, 10%–30%) to give 5-methoxycarbonyl-1,6-dihydro-2-methoxy-4-methoxymethyl-6-(3,4-difluorophenyl)pyrimidine as a pale yellow oil (4.3 g, 47%).

c) 5-Methoxycarbonyl-4-methoxymethyl-1,6-dihydro-2-methoxy-6-(3,4-difluorophenyl)-1-[(4-nitrophenyloxy)carbonyl]pyrimidine (Scheme 3; Step B)

To a well stirred solution of 5-methoxycarbonyl-1,6-dihydro-2-methoxy-4-methoxymethyl-6-(3,4-difluoro phenyl)pyrimidine (4.3 g, 13.18 mmol) and 4-(N,N-dimethylamino)pyridine (2.09 g, 17.13 mmol) in $CH_2Cl_2$ (100 mL) was added solid 4-nitrophenyl chloroformate (3.45 g, 17.13 mmol) at 0° C. The reaction mixture was stirred for 12 h at room temperature and the solid formed was removed by filtration. Solvent was evaporated from the filtrate and the residue was purified by column chromatography ($SiO_2$, dichloromethane/hexane, 20%–50%) to yield the product as a viscous oil (3.85 g, 59%).

d) 5-Methoxycarbonyl-4-methoxymethyl-1,6-dihydro-1-{N-[2-phenyl)ethyl]}carboxamido-2-methoxy-6-(3,4-difluorophenyl)pyrimidine (Scheme 3; Steps C-1 & C-2)

To a stirred solution of 5-methoxycarbonyl-4-methoxymethyl-1,6-dihydro-2-methoxy-6-(3,4-difluorophenyl)-1-[(4-nitrophenyloxy)carbonyl]pyrimidine (3.82 g, 7.77 mmol) in THF (140 mL) was added R-(+)-α-methylbenzylamine (1.13 g, 9.33 mmol, 1.2 eq.) at room temperature and the stirring was continued for 12 h. Solvent was evaporated and the residue was purified by column chromatography ($SiO_2$, 10–20% EtOAc in hexane). The first major product to elute was (+)-5-methoxycarbonyl-4-methoxmethyl-1,6-dihydro-1-{N-[2-phenyl)ethyl]}carboxamido-2-methoxy-6-(3,4-difluorophenyl)pyrimidine (1.74 g, 44.50%), as an oil. $[\alpha]_D$=+205.5 (c=5.1 g in 100 mL $CHCl_3$).

e) (+)-5-Methoxycarbonyl-1,6-dihydro-2-methoxy-4-methoxymethyl-6-(3,4-difluorophenyl)pyrimidine (Scheme 3; Step C-3)

To a stirred solution of (+)-5-methoxycarbonyl-4-methoxymethyl-1,6-dihydro-1-{N-[2-phenyl)ethyl]}carboxamido-2-methoxy-6-(3, 4-difluorophenyl)pyrimidine (1.74 g, 3.67 mmol) in toluene (40 mL) was added 1,8-diazabicyclo[5,4,0]-undec-7-ene (0.250 g, 1.64 mmol) and the mixture was stirred at 70–80° C. for 1.5 h. Solvent was evaporated and the residue was purified by flash column chromatography on silica gel with 9:1 $CHCl_3$/

EtOAc as eluent to give (+)-5-methoxycarbonyl-1,6-dihydro-2-methoxy-4-methoxymethyl-6-(3,4-difluoro phenyl)pyrimidine as a viscous oil (1.11 g, 92.5%).

f) Chiral HPLC separation of (+)-5-Methoxycarbonyl-1,6-dihydro-2-methoxy-4-methoxymethyl-6-(3,4-difluorophenyl)pyrimidine (Scheme 3; Step A)

The racemic 5-methoxycarbonyl-1,6-dihydro-2-methoxy-4-methoxymethyl-6-(3,4-difluorophenyl)pyrimidine was resolved by chiral HPLC [Chiralcel OD 20×250 mm #369–703–30604; λ 254 nm; hexanes/ethanol 95/5 and 0.01% diethylamine; 60 mg per injection; retention time of the desired enantiomer: 10.80 min., the first enantiomer peak to elute] to give (+)-5-methoxycarbonyl-1,6-dihydro-2-methoxy-4-methoxymethyl-6-(3,4-difluorophenyl)pyrimidine.

g) (+)-5-Methoxycarbonyl-4-methoxymethyl-1,6-dihydro-2-methoxy-6-(3,4-difluorophenyl)-1-[(4-nitrophenyl oxy)carbonyl]pyrimidine (Scheme 2; Step E)

To a well stirred solution of (+)-5-methoxycarbonyl-1,6-dihydro-2-methoxy-4-methoxymethyl-6-(3,4-difluorophenyl)pyrimidine (1.11 g, 3.4 mmol) and 4-(N,N-dimethylamino)pyridine (0.54 g, 4.42 mmol) in $CH_2Cl_2$ (200 mL) was added powdered 4-nitrophenyl chloroformate (0.891 g, 4.42 mmol) at room temperature. Solvent was evaporated and the residue was purified by column chromatography on silica gel using $CHCl_3$/EtOAc (20%–50%) as the eluent to give (+)-5-methoxycarbonyl-4-methoxymethyl-1,6-dihydro-2-methoxy-6-(3,4-diflurophenyl)-1-[(4-nitrophenyloxy)carbonyl]pyrimidine (1.30 g, 78%) as a viscous oil. $[\alpha]_D$=+262.2 (c=2.3 g in 100 mL $CHCl_3$).

h) (+)-5-Methoxycarbonyl-4-methoxymethyl-1,2,3,6-tetrahydro- 2-oxo-6-(3,4-difluorophenyl)-1-[(4-nitrophenyloxy)carbonyl]pyrimidine (Scheme 2; Step F)

To a solution of (+)-6-(3,4-difluorophenyl)-1,6-dihydro-2-methoxy-5-methoxycarbonyl-4-methoxymethyl-1-(4-nitrophenoxy)-carbonylpyrimidine (0.305 g, 0.60 mmol) in dichloromethane (15 mL), 1 N HCl in ether (6 mL) was added at room temperature and the mixture was stirred at room temperature for 12 hours. Solvent was evaporated at reduced pressure and the residue was dried to give 0.295 g (100%) of the product as a white powder.

Part 3 i) (+)-cis-6-(3,4-Difluorophenyl)-1-{N-[2-(4-cyano-4-phenyl-cyclohexylamino)ethyl]}carboxamido-5-methoxycarbonyl-4-methoxymethyl-2-oxo-1,2,3,6-tetrahydropyrimidine hydrochloride (Scheme 2; Step G)

A solution of (+)-5-methoxycarbonyl-4-methoxymethyl-1,2,3,6-tetrahydro-2-oxo-6-(3,4-difluorophenyl)-1-[(4-nitrophenyloxy)carbonyl]pyrimidine (0.850 g, 1.73 mmol) and cis-2-(4-cyano-4-phenyl-cyclohexylamino)ethylamine (0.567 g, 2.42 mmol) in dichloromethane (50 mL) was stirred at room temperature for 12 hours. It was washed with ice-cold 0.5 N NaOH (2×10 mL) and dried over sodium sulfate. Solvent was evaporated at reduced pressure and the residue was purified by flash chromatography on silica gel (dichloromethane:MeOH:2M ammonia in MeOH, 90:8:4) to give 0.905 g (90%) as a white powder. The HCl salt was prepared by treatment of a solution of the free base in ether with 1 N HCl in ether. The white powder was dried and recrystallized from anhydrous isopropanol. M.P. 233–235° C.; $[\alpha]_D$=+131.16(c=0.735, MeOH); Anal. Calcd. for $C_{30}H_{34}N_5O_5F_2Cl$: C, 58.30; H, 5.53; N, 11.06. Found: C, 57.91; H, 5.53; N, 11.10.

EXAMPLE 5

(+)-trans-6-(3,4-Difluorophenyl)-1-{N-[2-(4-cyano-4-phenyl-cyclohexylamino)ethyl]}carboxamido-5-methoxycarbonyl-4-methoxymethyl-2-oxo-1,2,3,6-tetrahydropyrimidine hydrochloride (Scheme 2; Step F)

A solution of (+)-5-methoxycarbonyl-4-methoxymethyl-1,2,3,6-tetrahydro-2-oxo-6-(3,4-difluorophenyl)-1-[(4-nitrophenyloxy)carbonyl]pyrimidine (0.850 g, 1.73 mmol) and trans-2-(4-cyano-4-phenyl-cyclohexylamino)ethylamine (0.567 g, 2.42 mmol) in dichloromethane (50 mL) was stirred at room temperature for 12 hours. It was washed with ice-cold 0.5 N NaOH (2×10 mL) and dried over sodium sulfate. Solvent was evaporated at reduced pressure and the residue was purified by flash chromatography on silica gel (dichloromethane:MeOH:2M ammonia in MeOH, 90:8:4) to give 0.905 g (90%) as a white powder. The HCl salt was prepared by treatment of a solution of the free base in ether with 1 N HCl in ether. Anal. Calcd. for $C_{30}H_{34}N_5O_5F_2Cl$:C, 58.30; H, 5.53; N, 11.06. Found: C, 57.99; H, 5.73; N, 11.20.

EXAMPLE 6

(−)-cis-6-(3,4-Difluorophenyl)-1-{N-[2-(4-cyano-4-phenyl-cyclohexylamino)ethyl]}carboxamido-5-methoxycarbonyl-4-methoxymethyl-2-oxo-1,2,3,6-tetrahydropyrimidine hydrochloride a) (−)-5-Methoxycarbonyl-4-methoxymethyl-1,6-dihydro-2-methoxy-6-(3,4-difluorophenyl)-1-[(4-nitrophenyloxy)carbonyl]pyrimidine (Scheme 2; Step E)

To a well stirred solution of (+)-5-methoxycarbonyl-1,6-dihydro-2-methoxy-4-methoxymethyl-6-(3,4-difluorophenyl)pyrimidine (1.167 g, 3.576 mmol) and 4-(N,N-dimethylamino)pyridine (0.655 g, 5.364 mmol) in $CH_2Cl_2$ (20 mL) was added powdered 4-nitrophenyl chloroformate (0.937 g, 4.65 mmol) at room temperature. Solvent was evaporated and the residue was purified by column chromatography on silica gel using hexanes/EtOAc (7/3%) as the eluent to give (−)-5-methoxycarbonyl-4-methoxymethyl-1,6-dihydro-2-methoxy-6-(3,4-diflurophenyl)-1-[(4-nitrophenyloxy)carbonyl]pyrimidine (1.761 g, 100%) as a viscous oil. $[\alpha]_D$=−335.3 (c=1.0 g in 100 mL $CHCl_3$).

b) (−)-cis-6-(3,4-Difluorophenyl)-1-{N-[2-(4-cyano-4-phenylcyclohexylamino)ethyl]}carboxamido-5-methoxycarbonyl-4-methoxymethyl-2-oxo-1,2,3,6-tetrahydropyrimidine hydrochloride (Scheme 2; G & Step F)

A solution of (−)-5-methoxycarbonyl-4-methoxymethyl-1,6-dihydro-2-methoxy-6-(3,4-difluorophenyl)-1-[(4-nitrophenyloxy)carbonyl]pyrimidine (0.103 g, 0.21 mmol) and cis-2-(4-cyano-4-phenyl-cyclohexylamino)ethylamine (0.059 g, 0.251 mmol) in dichloromethane (50 mL) was stirred at room temperature for 12 hours. It was washed with ice-cold 0.5 N NaOH (2×10 mL) and dried over sodium sulfate. Solvent was evaporated at reduced pressure and the residue was purified by flash chromatography on silica gel (dichloromethane:MeOH:2M ammonia in MeOH, 90:8:4) to give 0.121 g (100%) as an oil. It was dissolved in THF (2 mL), treated with 0.2 mL of 6 N HCl and stirred at room temperature for 4 h. Solvent was evaporated and the residue was dried in vacuo to give the product as a white powder (130 mg, 100%). M.P. 220–222° C.; $[\alpha]_D$=−124.29 (c=0.535, MeOH); Anal. Calcd. for $C_{30}H_{34}N_5O_5F_2Cl$: C, 58.30; H, 5.53; N, 11.06. Found: C, 57.20; H, 5.57; N, 11.30.

EXAMPLE 7

(+)-trans-6-(3,4-Difluorophenyl)-1-{N-[2-(4-(2-pyridyl)-cyclohexylamino)ethyl]}carboxamido-5-methoxycarbonyl-4-methoxymethyl-2-oxo-1,2,3,6-tetrahydropyrimidine hydrochloride a) General procedure for 2-[4-arylcyclohexylamino]ethylamine (Scheme 2; Step A)

A mixture of 4-arylcyclohexanone (48.7 mmol) (i.e. 4-(2-pyridyl)-cyclohexanone) and ethylenediamine (8.78 g, 146 mmol) and p-toluenesulfonic acid (92 mg) in benzene (200 mL) was refluxed for 4 h in Dean-Stark trap to remove the water that formed. Solvent was evaporated and the residue was redissolved in methanol (60 mL) and cooled to 0° C. To this, sodium borohydride (6.4 5 g) was added in portions and the mixture was stirred at room temperature for 3 h. Solvent was evaporated, the residue was dissolved in dichloromethane (300 mL), washed with brine (3×500 mL), dried (potassium carbonate), and the solvent evaporated to leave the product as a pale yellow viscous oil (90–95%). The product was pure and found to contain the cis/trans isomers. A careful chromatography of this mixture with chloroform/methanol/2M ammonia in methanol (100/10/5 to 100/20/10) gave some earlier fractions enriched in the cis isomer. The fractions eluted at the end were almost pure trans isomer.

b) (+)-trans-6-(3,4-Difluorophenyl)-1-{N-[2-(4-(2-pyridyl)-cyclohexylamino)ethyl]}carboxamido-5-methoxycarbonyl-4-methoxymethyl-2-oxo-1,2,3,6-tetrahydropyrimidine hydrochloride (Scheme 2; Step G)

A solution of (+)-5-methoxycarbonyl-4-methoxymethyl-1,2,3,6-tetrahydro-2-oxo-6-(3,4-difluorophenyl)-1-[(4-nitrophenyloxy)carbonyl]pyrimidine (49.1 mg, 0.1 mmol) and trans-2-(4-(2-pyridylcyclohexylamino)ethylamine (30 mg, 0.136 mmol) in THF (10 mL) was stirred at room temperature for 12 hours. It was washed with ice-cold 0.5 N NaOH (2×5 mL) and dried over sodium sulfate. Solvent was evaporated at reduced pressure and the residue was purified by preparative tlc on silica gel (ethyl acetate:MeOH, 10:1) to give 43 mg (78%) as a white powder. The HCl salt was prepared by treatment of a solution of the free base in ether with 1 N HCl in ether. 180–184° C.; $[\alpha]_D$=+186 (c =0.65, methanol); Anal. Calcd. for $C_{28}H_{35}N_5O_5F_2Cl_2.0.4CH_2Cl_2$:C, 51.33; H, 5.43; N, 9.54. Found: C, 51.31; H, 5.43; N,9.69.

EXAMPLES 8 AND 9 cis-6-(3,4-Difluorophenyl)-1-{N-[2-(4-phenyl-cyclohexylamino)ethyl]}carboxamido-5-methoxycarbonyl-4-methyl-2-oxo-1,2,3,6-tetrahydropyrimidine hydrochloride and
trans-6-(3,4-Difluorophenyl)-1-{N-[2(4-phenylcyclohexylamino)ethyl]}carboxamido-5-methoxycarbonyl-4-methyl-2-oxo-1,2,3,6-tetrahydro pyrimidine hydrochloride a) 2-[4-Phenylcyclohexylimino]ethylamine (Scheme 5; Step A)

A mixture of 4-phenylcyclohexanone (4.00 g, 22.96 mmol) and ethylenediamine (1.66 g, 27.5 mmol) and p-toluenesulfonic acid (437 mg) in benzene (200 mL) was refluxed for 4 h in Dean-Stark trap to remove the water that formed. Tlc analysis indicated the completion of the reaction. Solvent was evaporated and the product was used in the next step without any further purification.

b) cis-6-(3,4-Difluorophenyl)-1-{N-[2-(4-phenylcyclohexylamino)ethyl]}carboxamido-5-methoxycarbonyl-4-methyl-2-oxo-1,2,3,6-tetrahydropyrimidine hydrochloride and
trans-6-(3,4-Difluorophenyl)-1-{N-[2-(4-phenylcyclohexylamino)ethyl]}carboxamido-5-methoxycarbonyl-4-methyl-2-oxo-1,2,3,6-tetrahydropyrimidine hydrochloride (Scheme 5; Step B)

A solution of 5-methoxycarbonyl-4-methyl-1,2,3,6-tetrahydro-2-oxo-6-(3,4-difluorophenyl)-1-[(4-nitrophenyloxy)carbonyl]pyrimidine (120 mg, 0.269 mmol) and 2-[4-phenyl-cyclohexylimino]ethylamine (69.8 mg, 0.33 mmol) in dichloromethane (20 mL) was stirred at room temperature for 12 hours. Solvent was evaporated, the residue was redissolved in ethanol (10 mL) and cooled to 0° C. To this sodium borohydride (61 mg, 1.614 mmol) was added and the stirring continued for 2 h. Solvent was evaporated and the residue was purified by preparative tlc on silica gel using (dichloromethane:MeOH:2M ammonia in MeOH, 100:8:4) as eluent. Two products were isolated, the upper band corresponds to cis-6-(3,4-Difluorophenyl)-1-{N-[2-(4-phenyl-cyclohexylamino)ethyl]}carboxyamido-5-methoxycarbonyl-4-methyl-2-oxo-1,2,3,6-tetrahydropyrimidine (16 mg), and the lower band to trans-6-(3,4-Difluorophenyl)-1-{N-[2-(4-phenylcyclohexylamino)ethyl]}carboxamido-5-methoxycarbonyl-4-methyl-2-oxo-1,2,3,6-tetrahydropyrimidine (42 mg). The HCl salts were prepared by treatment of a solution of the free base in ether with 1 N HCl in ether.

Example 8

The cis isomer: M.P 145–146° C.; Anal. Calcd. for $C_{28}H_{33}N_4O_4F_2Cl$ $0.8H_2O$:C, 58.24; H, 6.04; N, 9.70. Found: C, 58.13; H, 5.83; N, 9.50.

Example 9

The trans isomer: M.P 156–157° C.; Anal. Calcd. for $C_{28}H_{33}N_4O_4F_2Cl$ $0.4CHCl_3$:C, 55.85; H, 5.51; N, 9.17. Found: C, 55.57; H, 5.76; N, 9.10.

EXAMPLE 10 trans-6-(3,4-Difluorophenyl)-1-{N-[2-[(4-phenylcyclohexyl)-methyl-amino]ethyl]}carboxamido-5-methoxycarbonyl-4-methyl-2-oxo-1,2,3,6-tetrahydropyrimidine hydrochloride (Scheme 5; Step C)

A mixture of trans-6-(3,4-difluorophenyl)-1-{N-[2-(4-phenyl-cyclohexylamino)ethyl]}carboxamido-5-methoxycarbonyl-4-methyl-2-oxo-1,2,3,6-tetrahydropyrimidine (60 mg, 0.114 mmol), methyl iodide (19.4 mg, 0.137 mmol, 1.2 eq.), and potassium carbonate (31.5 mg, 0.23 mmol) in acetone (10 mL) was stirred and refluxed for 12 h and the solid was removed by filtration. Solvent was evaporated from the filtrate and the residue was purified by flash chromatography on silica gel (dichloromethane:MeOH:2M ammonia in MeOH, 90:8:4) to give the product as an oil. The HCl salt was prepared by treatment of a solution of the free base in ether with 1 N HCl in ether (14 mg). M.P. 140–142° C.; Anal. Calcd. for $C_{29}H_{35}N_4O_4F_2Cl.0.33hexanes.0.59CHCl_3$:C, 56.07; H, 5.99; N, 8.28. Found: C, 56.37; H, 6.21; N, 7.90.

EXAMPLE 11

(+)-cis-6-(3,4-Difluorophenyl)-1-{N-[2-(4-methoxycarbonyl-4-phenyl-cyclohexylamino)ethyl]}carboxamido-5-methoxycarbonyl-4-methoxymethyl-2-oxo-1,2,3,6-tetrahydropyrimidine hydrochloride a) 2-[4-Methoxycarbonyl-4-phenyl-cyclohexylamino]ethylamine (Scheme 2; Step B)

A mixture of 2-[4-cyano-4-phenylcyclohexylamino]ethylamine (2.34 g, 10 mmol) and concentrated sulfuric acid (20 mL) was heated at 80–85° C. for 10 h. It was cooled to room temperature, mixed with anhydrous methanol (200 mL), and refluxed for 20 h. Solvent was evaporated and the residue was poured onto ice (200 g) and basified to pH 11 by addition 6 N NaOH. It was extracted with dichloromethane (4×125 mL), dried (potassium carbonate) and solvent evaporated to leave the product as an oil (2.1 g, 76%). This product was a pure mixture of cis and trans isomers. It was used in the next step without any further purification.

b) (+)-cis-6-(3,4-Difluorophenyl)-1-{N-[2-(4-methoxycarbonyl-4-phenyl-cyclohexylamino)ethyl]

}carboxamido-5-methoxycarbonyl-4-methoxymethyl-2-oxo-1,2,3,6-tetrahydropyrimidine hydrochloride (Scheme 2; Step G)

A solution of (+)-5-methoxycarbonyl-4-methoxymethyl-1,2,3,6-tetrahydro-2-oxo-6-(3,4-difluorophenyl)-1-[(4-nitrophenyloxy)carbonyl]pyrimidine (128 mg, 0.26 mmol) and 2-(4-methoxcarbonyl-4-phenylcyclohexylamino)ethylamine (70 mg, 0.26 mmol) in dichloromethane (15 mL) was stirred at room temperature for 12 hours. It was washed with ice-cold 0.5 N NaOH (2×5 mL) and dried over sodium sulfate. Solvent was evaporated at reduced pressure and the residue was purified by flash chromatography on silica gel (dichloromethane:MeOH:2M ammonia in MeOH, 90:8:4) to give 78 mg (78%) as a white powder. The HCl salt was prepared by treatment of a solution of the free base in ether with 1 N HCl in ether. 112–114° C.; $[\alpha]_D$=+136 (c=0.55, CHCl$_3$); Anal. Calcd. for $C_{31}H_{37}N_4O_7F_2Cl 0.4CH_2Cl_2$ :C, 55.05; H, 5.56; N, 8.18. Found: C, 55.05; H, 5.50; N, 8.16.

EXAMPLE 12

(+)-6-(3,4-Difluorophenyl)-1-{N-[2-(4,4-diphenyl-cyclohexylamino)ethyl]}carboxamido-5-methoxycarbonyl-4-methoxymethyl-2-oxo-1,2,3,6-tetrahydropyrimidine hydrochloride a) 2-[4,4-Diphenylcyclohexylamino]ethylamine (Scheme 2; Step A)

A mixture of 4,4-diphenylcyclohexanone (2.5 g) and ethylenediamine (10 g) and p-toluenesulfonic acid (100 mg) in benzene (200 mL) was refluxed for 4 h in Dean-Stark trap to remove the water that formed. Solvent was evaporated and the residue was redissolved in methanol (60 mL) and cooled to 0° C. To this, sodium borohydride (2 g) was added in portions and the mixture was stirred at room temperature for 3 h. Solvent was evaporated, the residue was dissolved in dichloromethane (300 mL), washed with brine (3×500 mL), dried (potassium carbonate), and the solvent evaporated to leave the product as a colorless viscous oil (2.94 g, 100%). The $^1$H-NMR showed this product to be pure and was used in the next step without any further purification.

b) (+)-6-(3,4-Difluorophenyl)-1-{N-[2-(4,4-diphenylcyclohexylamino)ethyl]}carboxamido-5-methoxycarbonyl-4-methoxymethyl-2-oxo-1,2,3,6-tetrahydropyrimidine hydrochloride (Scheme 2; Step G)

A solution of (+)-5-methoxycarbonyl-4-methoxymethyl-1,2,3,6-tetrahydro-2-oxo-6-(3,4-difluorophenyl)-1-[(4-nitrophenyloxy)carbonyl]pyrimidine (125 mg, 0.254 mmol) and 2-(4,4-diphenylcyclohexylamino)ethylamine (125 mg, 0.446 mmol) in THF (15 mL) was stirred at room temperature for 12 hours. It was washed with ice-cold 0.5 N NaOH (2×5 mL) and dried over sodium sulfate. Solvent was evaporated at reduced pressure and the residue was purified by flash chromatography on silica gel (dichloromethane:MeOH:2M ammonia in MeOH, 90:8:4) to give 147 mg (92%) of the product as a white powder. The HCl salt was prepared by treatment of a solution of the free base in ether with 1 N HCl in ether. 160–162° C.; $[\alpha]_D$=+184 (c=0.68, methanol); Anal. Calcd. for $C_{35}H_{39}N_4O_5F_2Cl 0.19CH_2Cl_2$ :C, 61.68; H, 5.79; N, 8.18. Found: C, 62.82; H, 5.87; N, 8.37.

EXAMPLE 13

(+)-cis-6-(3,4-Difluorophenyl)-1-{N-[2-(4-cyano-4-(2-fluorophenyl)-cyclohexylamino)ethyl]}carboxamido-5-methoxycarbonyl-4-methyl-2-oxo- 1,2,3,6-tetrahydropyrimidine hydrochloride A mixture of (+)-6-(3,4-difluorophenyl)-1,6-dihydro-5-methoxycarbonyl-4-methyl-1-(4-nitro)phenoxycarbonyl-2-pyrimidone (60 mg, 0.138 mmol), cis-2-[4-cyano-4-(2-fluorophenyl)cyclohexylamino]ethylamine (50 mg, 0.19 mmol) and methylene chloride (4 mL) was stirred at room temperature overnight. After being washed with 1 N NaOH solution, the organic layer was concentrated and purified by preparative TLC (eluent: 10/1 ethyl acetate/2M ammonia in methanol) to give the title compound in 41% yield (32 mg) as a yellow foam: DCIMS, m/z=570 (MH$^+$). Treatment of the free base with 1 equivalent of 1M HCl in ether gave the HCl salt as an off-white solid: m.p. 172–176° C. $[\alpha]_D$=114.7 (1.9 mg/mL MeOH). Anal. Calc. for $C_{29}H_{30}F_3N_5O_4HCl 0.5CHCl_3$: C, 53.22; H, 4.77; N, 10.52. Found: C, 53.34; H, 4.77; N, 10.45.

EXAMPLE 14

(+)-cis-6-(3,4-Difluorophenyl)-1-{N-[2-(4-cyano-4-(2-pyridyl)-cyclohexylamino)ethyl]}carboxamido-5-methoxycarbonyl-4-methoxymethyl-2-oxo-1,2,3,6-tetrahydropyrimidine hydrochloride (Scheme 2; Step G)

A mixture of (+)-6-(3,4-difluorophenyl)-1,6-dihydro-5-methoxycarbonyl-4-methoxymethyl-1-(4-nitro)phenoxycarbonyl-2-pyrimidone (50 mg, 0.107 mmol), cis-2-[4-cyano-4-(2-pyridyl)cyclohexylamino]ethylamine (40 mg, 0.164 mmol) and methylene chloride (4 mL) was stirred at room temperature overnight. After being washed with 1 N NaOH solution, the organic layer was concentrated and purified by preparative TLC (eluent: 10/1 ethyl acetate/2M ammonia in methanol) to give the title compound in 50% yield (31 mg) as a yellow oil: CIMS, m/z=583 (MH$^+$). Treatment of the free base with 2 equivalents of 1M HCl in ether gave the HCl salt as an off-white solid: m.p. 148–152° C. $[\alpha]_D$=110.9 (1.65 mg/mL MeOH). Anal. Calc. for $C_{29}H_{32}F_2N_6O_5 2HCl 0.65CHCl_3$: C, 48.58; H, 4.76; N, 11.46. Found: C, 48.30; H, 4.87; N, 11.20.

EXAMPLE 15 cis-6-(3,4-Difluorophenyl)-1-{N-[3-(4-cyano-4-phenyl-cyclohexylamino)propyl]}carboxamido-5-methoxycarbonyl-4-methyl-2-oxo-1,2,3,6-tetrahydropyrimidine hydrochloride a) General procedure for 3-[4-Cyano-4-arylcyclohexylamino]propylamine a) 3-[4-Cyano-4-phenylcyclohexylamino]propylamine (Scheme 6; Step A)

A mixture of 4-cyano-4-phenylcyclohexanone (5.0 g, 25.09 mmol) and 1,3-diaminopropane (5.58 g, 75.3 mmol) and p-toluenesulfonic acid (23 mg) in benzene (50 mL) was refluxed for 4 h in Dean-Stark trap to remove the water that formed. Solvent was evaporated and the residue was redissolved in methanol (40 mL) and cooled to 0° C. To this, sodium borohydride (6.4 5 g) was added in portions and the mixture was stirred at room temperature for 3 h. Solvent was evaporated, the residue was dissolved in dichloromethane (300 mL), washed with brine (3×500 mL), dried (potassium carbonate), and the solvent evaporated to leave the product as a pale yellow viscous oil (4.5 g, 72%). The $^1$H-NMR showed this product to be pure and found to contain the cis/trans isomers in the ratio of about 4:1.

b) cis-6-(3,4-Difluorophenyl)-1-{N-[3-(4-cyano-4-phenyl-cyclohexylamino)propyl]}carboxamido-5-methoxycarbonyl-4-methyl-2-oxo-1,2,3,6-tetrahydropyrimidine hydrochloride (Scheme 6; Step B)

A solution of 5-methoxycarbonyl-4-methyl-1,2,3,6-tetrahydro-2-oxo-6-(3,4-difluorophenyl)-1-[(4-nitrophenyloxy)carbonyl]pyrimidine (0.500 g, 1.15 mmol) and 3-[4-cyano-4-phenylcyclohexylamino]propylamine (0.371 g, 1.49 mmol) in dichloromethane (50 mL) was stirred at room temperature for 12 hours. It was washed with ice-cold 0.5 N NaOH (2×10 mL) and dried over sodium sulfate. Solvent was evaporated at reduced pressure and the residue was purified by flash chromatography on silica gel (dichloromethane:MeOH:2M ammonia in MeOH, 90:8:4) to give 0.570 g (87.6%) of the product as a white powder. The HCl salt was prepared by treatment of a solution of the free base in ether with 1 N HCl in ether. M.p. 163–165° C.; Anal. Calcd. for $C_{30}H_{34}N_5O_4F_2Cl.1.2H_2O$: C, 57.77; H, 5.88; N, 11.23. Found: C, 57.65; H, 5.71; N, 11.20.

EXAMPLE 16

(+)-cis-1-3-{[4-(3,4-Difluorophenyl)-2,5-dioxo-1,2,3,4,5,7-hexahydro-4H-furo[3,4-d]-pyrimidine-3-carbonyl]amino}-ethyl-(4-cyano-4-phenylcyclohexyl)amine hydrochloride a) (+)-6-(3,4-Difluorophenyl)-1,6-dihydro-2-oxo-5-methoxy-carbonyl-4-bromomethyl-1-[(4-nitrophenyl-oxy)carbonyl]pyrimidine (Scheme 7; Step A)

To a well stirred solution of (+)-6-(3,4-difluorophenyl)-1,6-dihydro-2-methoxy-5-methoxycarbonyl-4-methyl-1-[(4-nitrophenyloxy)carbonyl]pyrimidine (1.5 mmol, 0.66 g) in 5 mL of chloroform was added a solution of bromine (1.5 mmol, 0.09 mL) in 3 mL of chloroform at 0° C. and the solution was allowed to attain room temperature over 1.5 h. The solvent was removed in vacuo and the residue was again dissolved in $CHCl_3$ (20 mL) and washed with brine. The organic layer was separated, dried over $Na_2SO_4$, filtered and the solvent was removed in vacuo to get 0.81 g of (+)-6-(3,4-difluorophenyl)-1,6-dihydro-2-oxo-5-methoxycarbonyl-4-bromomethyl-1-[(4-nitrophenyloxy)carbonyl]pyrimidine as a yellow foam. It was used in the next step without any purification.

b) (+)-4-(3,4-Difluorophenyl)-2,5-dioxo-1,2,4,5,6,7-hexahydro-cyclopentapyrimidine-3-carboxylic acid-4-nitrophenyl ester (Scheme 7; Step B)

(+) -6-(3,4-Difluorophenyl)-1,6-dihydro-2-oxo-5-methoxy-carbonyl-4-bromomethyl-1-[(4-nitrophenyloxy)carbonyl]pyrimidine (1.5 mmol, 0.81 g) was heated in oil bath for 3 h (bath temperature 130° C. The brown residue thus obtained was washed with $CHCl_3$ and (+)-4-(3,4-difluoro-phenyl)-2,5-dioxo-1,2,4,5,6,7-hexahydro-cyclopentapyrimidine-3-carboxylic acid-4-nitrophenyl ester was obtained as a pale brown solid which was used in the next step without further purification (crude wt. 0.51g).

c) (+)-cis-1-3-{[4-(3,4-Difluorophenyl)-2,5-dioxo-1,2,3,4,5,7-hexahydro-4H-furo[3,4-d]-pyrimidine-3-carbonyl]amino}-ethyl-(4-cyano-4-phenylcyclohexyl)amine hydrochloride (Scheme 7; Step C)

A solution of (+)-4-(3,4-difluorophenyl)-2,5-dioxo-1,2,4,5,6,7-hexahydro-cyclopenta pyrimidine-3-carboxylic acid-4-nitrophenyl ester (86 mg, 0.20 mmol) and cis-2-(4-cyano-4-phenylcyclohexylamino)ethylamine (70 mg, 0.3 mmol) in THF (5 mL) was stirred at room temperature for 12 hours. It was purified by preparative tlc on silica gel (ethyl acetate/methanol, 90:10) to give 91 mg (85%) as a white powder. The HCl salt was prepared by treatment of a solution of the free base in ether with 1 N HCl in ether. $[\alpha]_D$=+102 (c=0.75, MeOH); Anal. Calcd. for $C_{28}H_{27}N_5O_4F_2Cl.0.38CH_2Cl_2$: C, 56.41; H, 4.80; N, 11.59. Found: C, 56.80; H, 4.96; N, 11.29.

EXAMPLE 17

(+)-cis-6-(3,4-Difluorophenyl)-1-[4-(4-cyano-4-phenyl-cyclohexylamino)butyl]-5-methoxycarbonyl-2,4-dimethyl-1,6-dihydropyrimidine hydrochloride (Scheme 8)

To a suspension of NaH (50 mg, 60% dispersion in mineral oil) in THF (7 mL) was added a solution of 6-(3,4-difluorophenyl)-1,6-dihydro-5-methoxycarbonyl-2,4-dimethylpyrimidine (0.32 g, 1.14 mmol.) and HMPA (0.205 g, 1.14 mmol.) in THF (8 mL) at 0° C. After 15 min, 1,4-dibromobutane (0.47 mL, 4.0 mmol.) was added. The reaction mixture was then refluxed for 10 min. The solid was filtered off. After the removal of the solvent, the residue was flash chromatographed over silica gel (eluent: ethyl acetate) to give the product in 44% yield (0.2 g) as a yellow oil.

A mixture of 1-(4-bromobutyl)-6-(3,4-difluorophenyl)-1,6-dihydro-5-methoxycarbonyl-2,4-dimethylpyrimidine (0.1 g, 0.43 mmol), cis-4-cyano-4-phenylcyclohexylamine (0.18 g, 0.9 mmol), potassium carbonate (0.3 g, 2.1 mmol), sodium iodide (65 mg, 0.43 mmol) and acetone (6 mL) was refluxed overnight. After removal of the solid and solvent, the residue was purified by preparative TLC (eluent: 100/20 v/v ethyl acetate-2M ammonia in methanol) to give the product in quantitative yield (0.23 g) as a pair of diastereomers. HPLC separation (Column: Chiralcel OD 20×250 mm; Eluent: 60/40/0.1 hexane/2-propanol/diethylamine) gave the pure title compound as a yellow oil: DCIMS, m/z=535 (MH⁺). Treatment of the free base with 2 equivalents of 1M HCl in ether gave the HCl salt as a white solid: m.p. 169–172° C. $[\alpha]_D$=68.6 (2.2 mg/mL MeOH). Anal. Calc. for $C_{31}H_{36}F_2N_4O_2$·2HCl0.9CHCl_3: C, 53.59; H, 5.48; N, 7.84. Found: C, 53.61; H, 5.67; N, 7.81.

It is understood that additional compounds may be synthesized under the general synthetic schemes referred to herein using appropriately substituted starting materials.

EXAMPLE 18

As a specific embodiment of an oral composition of a compound of this invention, 100 mg of one of the compounds described herein is formulated with sufficient finely divided lactose to provide a total amount of 580 to 590 mg to fill a size O hard gel capsule.

Pharmacological Profiles of the Compounds in Cloned Human Adrenergic Receptors

Binding affinities were measured for selected compounds of the invention at six cloned human alpha-1 and alpha-2 receptor subtypes, as well as at the L-type calcium channel. The protocols for these experiments are given below.

Protocol for the Determination of the Potency of $\alpha_1$ Antagonists

The activity of compounds at the different human receptors was determined in vitro using cultured cell lines that selectively express the receptor of interest. These cell lines were prepared by transfecting the cloned cDNA or cloned genomic DNA or constructs containing both genomic DNA and cDNA encoding the human α-adrenergic receptors as follows:

$\alpha_{1D}$ Human Adrenergic Receptor

The entire coding region of $\alpha_{1D}$ (1719 bp), including 150 base pairs of 5' untranslated sequence (5' UT) and 300 bp of 3' untranslated sequence (3' UT), was cloned into the BamHI and ClaI sites of the polylinker-modified eukaryotic expression vector pCEXV-3, called EXJ.HR. The construct involved the ligation of partial overlapping human lymphocyte genomic and hippocampal cDNA clones: 5' sequence were contained on a 1.2 kb SmaI-XhoI genomic fragment (the vector-derived BamHI site was used for subcloning instead of the internal insert-derived SmaI site) and 3' sequences were contained on an 1.3 kb XhoI-ClaI cDNA fragment (the ClaI site was from the vector polylinker). Stable cell lines were obtained by cotransfection with the plasmid α1A/EXJ (expression vector containing the α1A receptor gene (old nomenclature)) and the plasmid pGCcos3neo (plasmid containing the aminoglycoside transferase gene) into LM(tk-) cells using calcium phosphate technique. The cells were grown, in a controlled environment (37° C., 5% $CO_2$), as monolayers in Dulbecco's modified Eagle's Medium (GIBCO, Grand Island, N.Y.)

containing 25 mM glucose and supplemented with 10% bovine calf serum, 100 units/ml penicillin g, and 100 μg/ml streptomycin sulfate. Stable clones were then selected for resistance to the antibiotic G-418 (1 mg/ml), and membranes were harvested and assayed for their ability to bind [$^3$H] prazosin as described below (see "Radioligand Binding assays").

The cell line expressing the human $\alpha_{1D}$ receptor used herein was designated L-$\alpha_{1A}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1D}$ receptor, was accorded ATCC Accession No. CRL 11138, and was deposited on Sep. 25, 1992.

$\alpha_{1B}$ Human Adrenergic Receptor

The entire coding region of a1B (1563 bp), including 200 base pairs and 5' untranslated sequence (5' UT) and 600 bp of 3' untranslated sequence (3' UT), was cloned into the EcoRI site of pCEXV-3 eukaryotic expression vector. The construct involved ligating the full-length containing EcoRI brainstem cDNA fragment from λ ZapII into the expression vector. Stable cell lines were selected as described above. The cell line used herein was designated L-$\alpha_{1B}$ and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line L-$\alpha_{1B}$ was accorded ATCC Accession No. CRL 11139, on Sep. 25, 1992.

$\alpha_{1A}$ Human Adrenergic Receptor

The entire coding region of $\alpha_{1A}$ (1401 bp), including 400 base pairs of 5' untranslated sequence (5' UT) and 200 bp of 3' untranslated sequence (3' UT), was cloned into the KpnI site of the polylinker-modified pCEXV-3-derived eukaryotic expression vector, EXJ.RH. The construct involved ligating three partial overlapping fragments: a 5' 0.6kb HincII genomic clone, a central 1.8 EcoRI hippocampal cDNA clone, and a 3' 0.6Kb PstI genomic clone. The hippocampal cDNA fragment overlaps with the 5' and 3' genomic clones so that the HincII and PstI sites at the 5' and 3' ends of the cDNA clone, respectively, were utilized for ligation. This full-length clone was cloned into the KpnI site of the expression vector, using the 5' and 3' KpnI sites of the fragment, derived from vector (i.e., pBluescript) and 3'-untranslated sequences, respectively. Stable cell lines were selected as described above. The stable cell line expressing the human $\alpha_{1A}$ receptor used herein was designated L-$\alpha_{1C}$ (old nomenclature) and was deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. The cell line expressing the human $\alpha_{1A}$ receptor was accorded Accession No. CRL 11140, on Sep. 25, 1992.

Radioligand Binding Assays

Transfected cells from culture flasks were scraped into 5 ml of 5 mM Tris-HCl, 5 mM EDTA, pH 7.5, and lysed by sonication. The cell lysates were centrifuged at 1000 rpm for 5 min at 4° C., and the supernatant was centrifuged at 30,000×g for 20 min at 4° C. The pellet was suspended in 50 mM Tris-HCl, 1 mM MgCl$_2$, and 0.1% ascorbic acid at pH 7.5. Binding of the α1 antagonist [$^3$H]prazosin (0.5 nM, specific activity 76.2 Ci/mmol) to membrane preparations of LM(tk-) cells was done in a final volume of 0.25 ml and incubated at 37° C. for 20 min. Nonspecific binding was determined in the presence of 10 μM phentolamine. The reaction was stopped by filtration through GF/B filters using a cell harvester. Inhibition experiments, routinely consisting of 7 concentrations of the tested compounds, were analyzed using a non-linear regression curve-fitting computer program to obtain Ki values.

$\alpha_2$ Human Adrenergic Receptors

To determine the potency of $\alpha_1$ antagonists at the $\alpha_2$ receptors, LM(tk-) cell lines stably transfected with the genes encoding the $\alpha_{2A}$, $\alpha_{2B}$ and $\alpha_{2C}$ receptors were used. The cell line expressing the $\alpha_{2A}$ receptor is designated L-$\alpha_{2A}$, and was deposited on Nov. 6, 1992 under ATCC Accession No. CRL 11180. The cell line expressing the $\alpha_{2B}$ receptor is designated L-NGC-$\alpha_{2B}$, and was deposited on Oct. 25, 1989 under ATCC Accession No. CRL10275. The cell line expressing the $\alpha_{2C}$ receptor is designated L-$\alpha_{2C}$, and was deposited on Nov. 6, 1992 under ATCC Accession No. CRL-11181. All the cell lines were deposited with the American Type Culture Collection, 12301 Parklawn Drive, Rockville, Md. 20852, U.S.A. under the provisions of the Budapest Treaty for the International Recognition of the Deposit of Microorganisms for the Purposes of Patent Procedure. Cell lysates were prepared as described above (see Radioligand Binding Assays), and suspended in 25 mM glycylglycine buffer (pH 7.6 at room temperature). Equilibrium competition binding assay were performed using [3H] rauwolscine (0.5nM), and nonspecific binding was determined by incubation with 10 μM phentolamine. The bound radioligand was separated by filtration through GF/B filters using a cell harvester.

Determination of the Activity of $\alpha_1$ Antagonists at Calcium Channels

The potency of $\alpha_1$ antagonists at calcium channels was determined in competition binding assays of [$^3$H] nitrendipine to membrane fragments of rat cardiac muscle, essentially as described by Glossman and Ferry (Methods in Enzymology 109:513–550, 1985). Briefly, the tissue was minced and homogenized in 50 mM Tris-HCl (pH 7.4) containing 0.1 mM phenylmethylsulfonyl fluoride. The homogenates were centrifuged at 1000 g for 15 minutes, the resulting supernatant was centrifuged at 45,000 g for 15 minutes. The 45,000 g pellet was suspended in buffer and centrifuged a second time. Aliquots of membrane protein were incubated for 30 minutes at 37° C. in the presence of [$^3$H]nitrendipine (1 nM), and nonspecific binding was determined in the presence of 10 μM nifedipine. The bound radioligand was separated by filtration through GF/B filters using a cell harvester.

The compounds described above were assayed using cloned human alpha adrenergic receptors and the rat calcium channel. The preferred compounds were found to be $\alpha_{1A}$ selective antagonists. The compounds described herein were also found to exhibit weak binding affinity to the rat L-type calcium channel. The alpha adrenergic receptor binding affinities of compounds 2–5, 7, 11, 13 and 14 are illustrated in Table 1 as follows:

TABLE 1

Binding affinities of selected compounds at cloned human alpha-1 adrenergic receptors

| | h$\alpha_{1D}$ | | | h$\alpha_{1B}$ | | | h$\alpha_{1A}$ | | |
|---|---|---|---|---|---|---|---|---|---|
| Example | pK$_i$ | SEM | n | pK$_i$ | SEM | n | pK$_i$ | SEM | n |
| 2 | 7.05 | 0.07 | 2 | 7.76 | 0.07 | 2 | 9.51 | 0.07 | 2 |
| 3 | 6.62 | 0.02 | 3 | 7.00 | 0.03 | 3 | 9.31 | 0.07 | 3 |

TABLE 1-continued

Binding affinities of selected compounds at cloned human alpha-1 adrenergic receptors

| Example | $h\alpha_{1D}$ | | | $h\alpha_{1B}$ | | | $h\alpha_{1A}$ | | |
|---|---|---|---|---|---|---|---|---|---|
| | $pK_i$ | SEM | n | $pK_i$ | SEM | n | $pK_i$ | SEM | n |
| 4 | 7.00 | 0.10 | 3 | 7.73 | 0.07 | 3 | 9.87 | 0.07 | 4 |
| 5 | 6.91 | 0.10 | 3 | 7.57 | 0.06 | 3 | 9.90 | 0.01 | 4 |
| 7 | 5.41 | 0.03 | 2 | 5.95 | 0.09 | 2 | 8.35 | 0.24 | 2 |
| 11 | 6.90 | 0.04 | 2 | 7.56 | 0.03 | 2 | 9.66 | 0.11 | 2 |
| 13 | 7.29 | 0.02 | 2 | 7.87 | 0.01 | 2 | 9.99 | 0.18 | 2 |
| 14 | 5.96 | 0.04 | 2 | 6.55 | 0.04 | 2 | 9.03 | 0.08 | 2 |

SCHEME 1

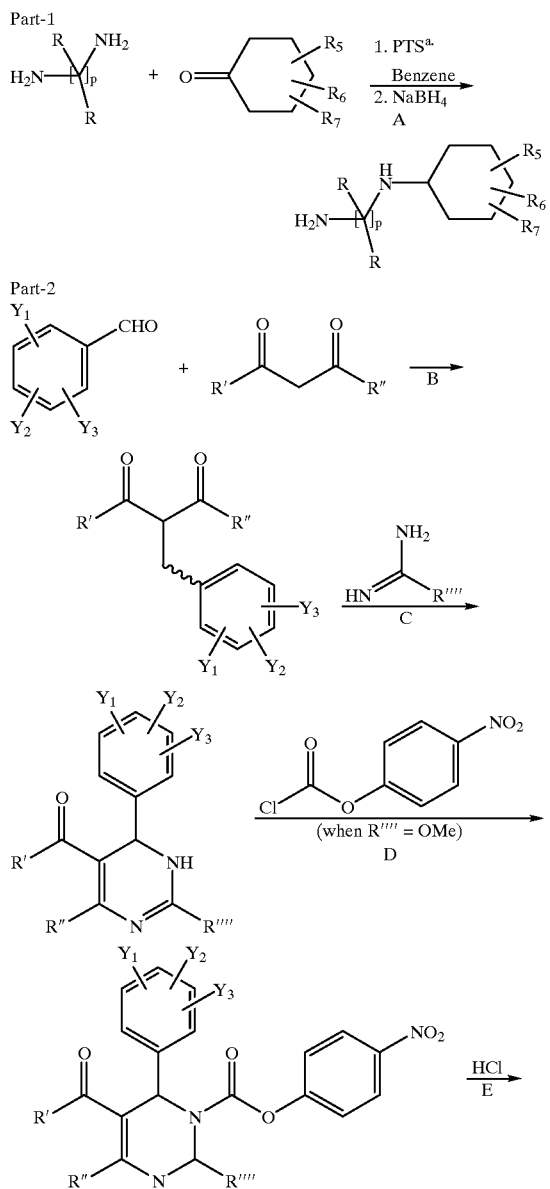

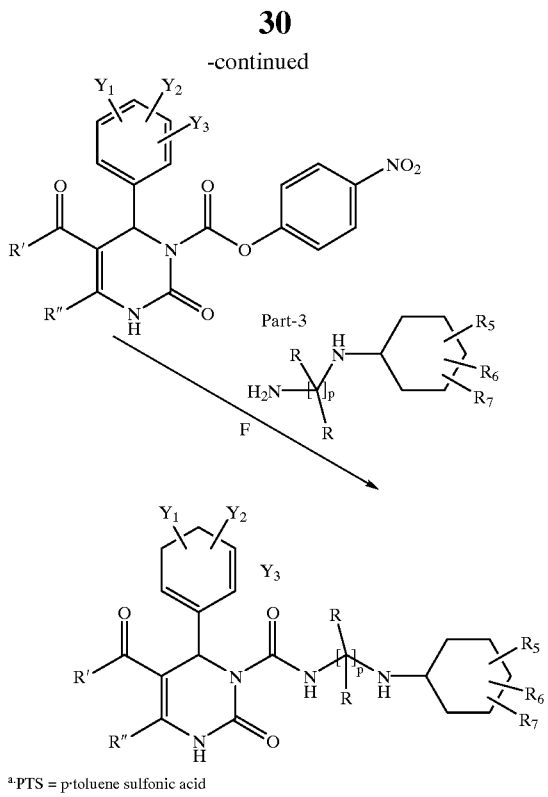

a. PTS = p-toluene sulfonic acid

In Part 1 of the general synthetic scheme, an optionally substituted cycloalkanone is refluxed with a diaminoalkane to form the corresponding (cycloalk-1-yl)aminoalkylimine, which on treatment with $NaBO_4$ yields (cycloalk-1-yl) aminoalkylamine. In part 3 the diamine is added to a 1-[(4-nitrophenyl)oxycarbonyl]pyrimidine to yield the final product. Although cyclohexanone is shown, the process is equally applicable to substituted cycloalkanones from cyclobutanone through cyclo-octanone. In addition, replacement of the diamino-alkane of Part 1 with an aminoalkanol yields esters in Part 3 instead of amides. In the schemes which follow, the diaminoalkane is shown for clarity as either ethyl, propyl or butyl; however, any suitable alkyl, branched alkyl or substituted alkyl as shown in Scheme 1 may be used, wherein R is as defined in the specification.

In Part 2 of the general synthetic scheme, it is important to note that the use of the O-methylisourea (R""=OMe) in Step D allows the production of several different 2-substituents on the dihydropyrimidine. In particular, addition of primary amines (i.e., $NH_2R_3$) to the 2-methoxy pyrimidines affords 2-amino pyrimidines. Alternatively, when R""=OMe is replaced with 4-methoxybenzylthiol, 2-thioxodihydropyrimidines may be produced by treatment of the product with ethanethiol and TFA.

SCHEME 2

Part-1

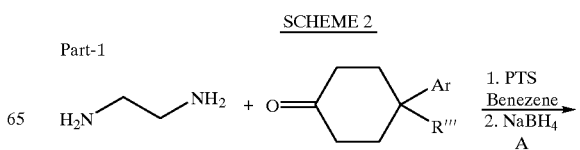

Part-2

R''' = H, CN, Ph[a.]
Ar = Ph, 2-pyridyl, 2-FPh

Ar = Ph, 2-pyridyl, 2-FPh
$Y_1 = Y_2 = F$; $Y_3 = F, H$
R' = MeO, BnO[b], Me
R'' = Me, Et, MeOCH$_2$
R''' = H, CN, CO$_2$Me, Ph
R'''' = OMe, Me

[a.]Ph = phenyl
[b.]Bn = benzyl

SCHEME 3
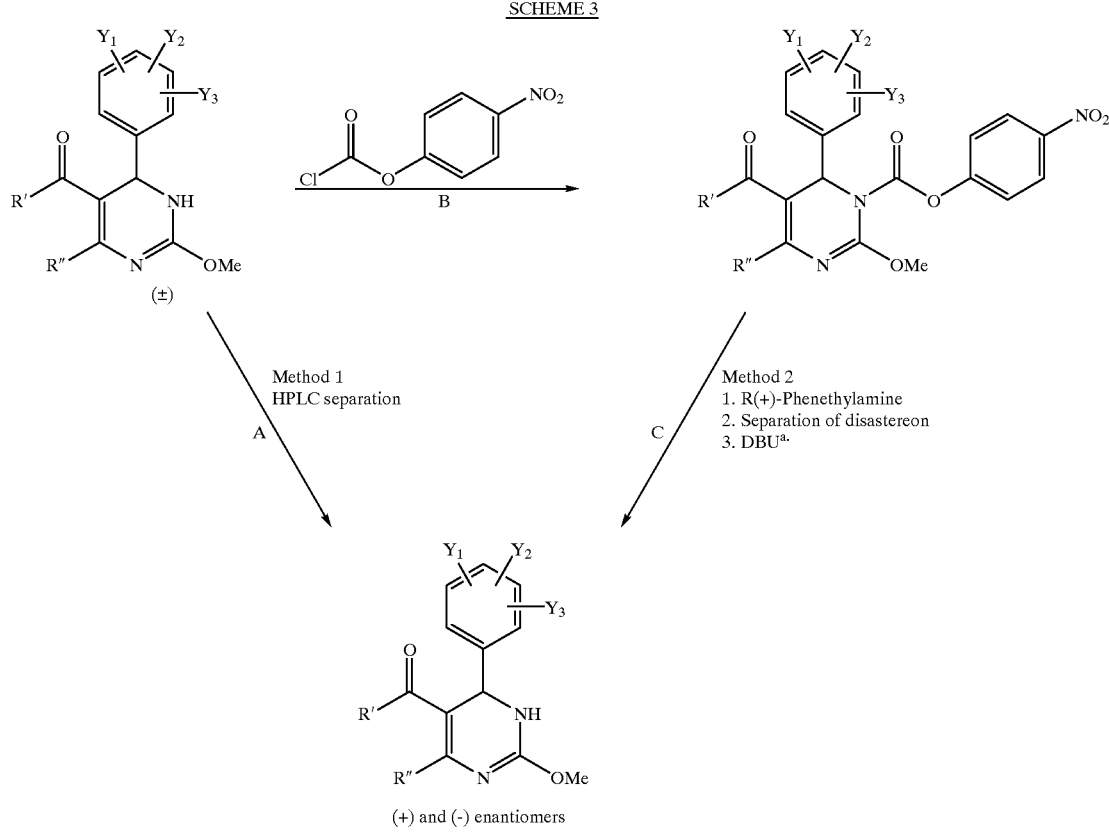
a. DBU = 1,8-diazabicyclo [5.4.0] undec-7-ene
SCHEME 4
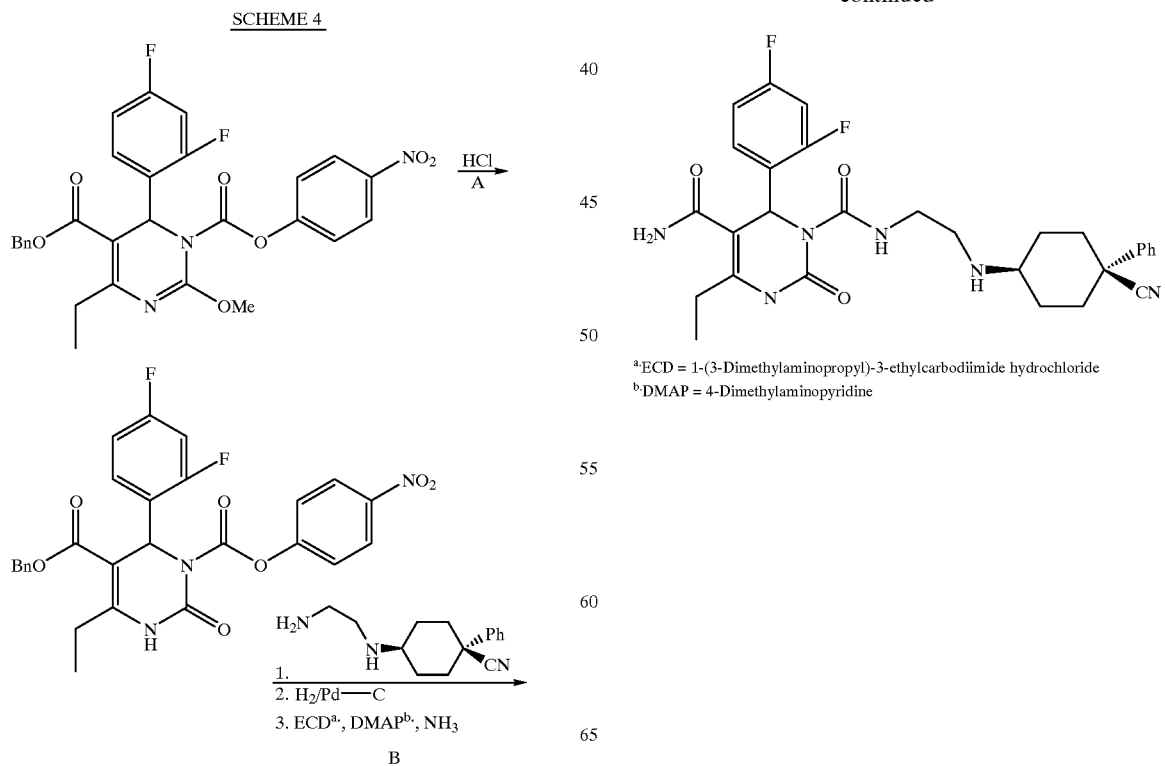
a. ECD = 1-(3-Dimethylaminopropyl)-3-ethylcarbodiimide hydrochloride
b. DMAP = 4-Dimethylaminopyridine

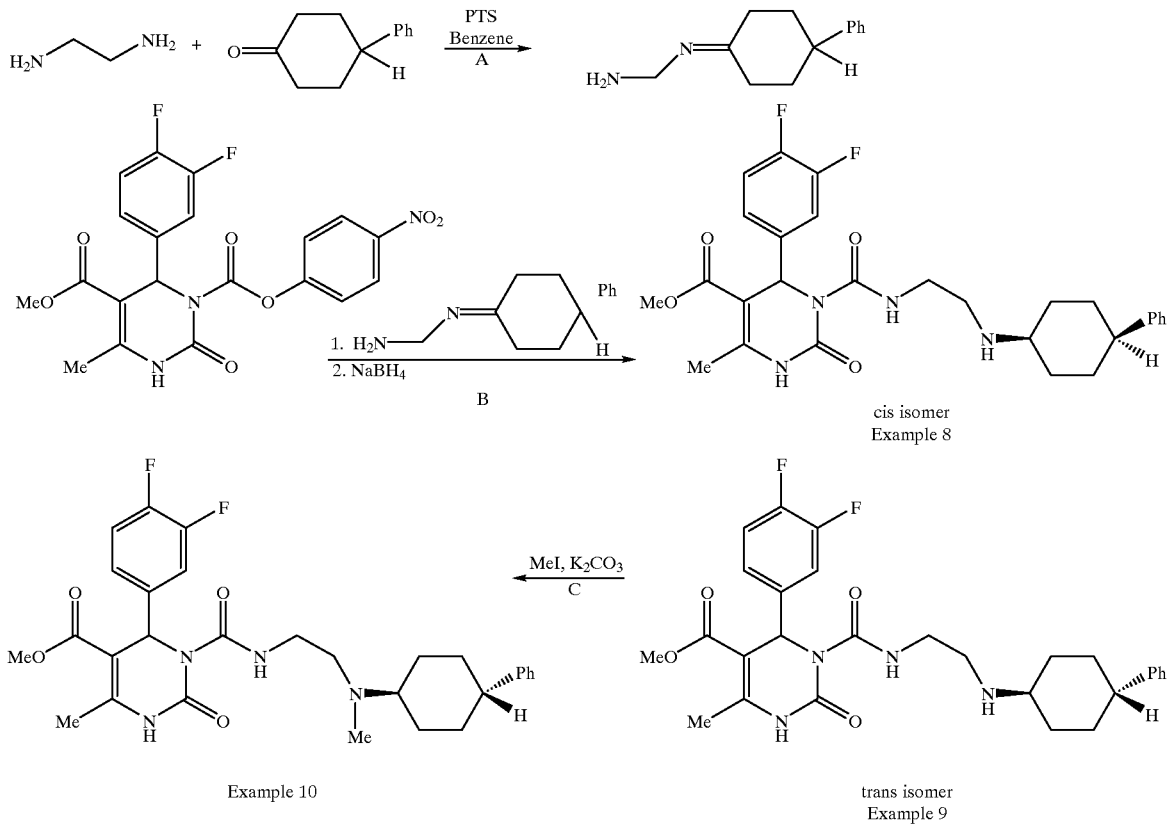
SCHEME 5
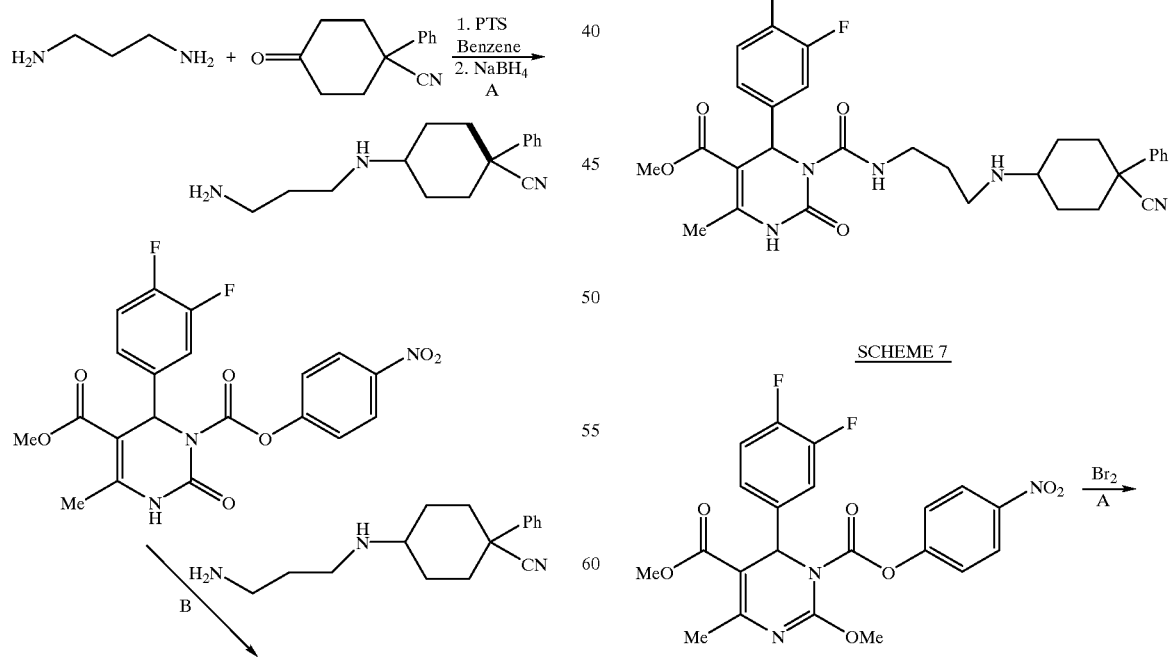
SCHEME 6
SCHEME 7

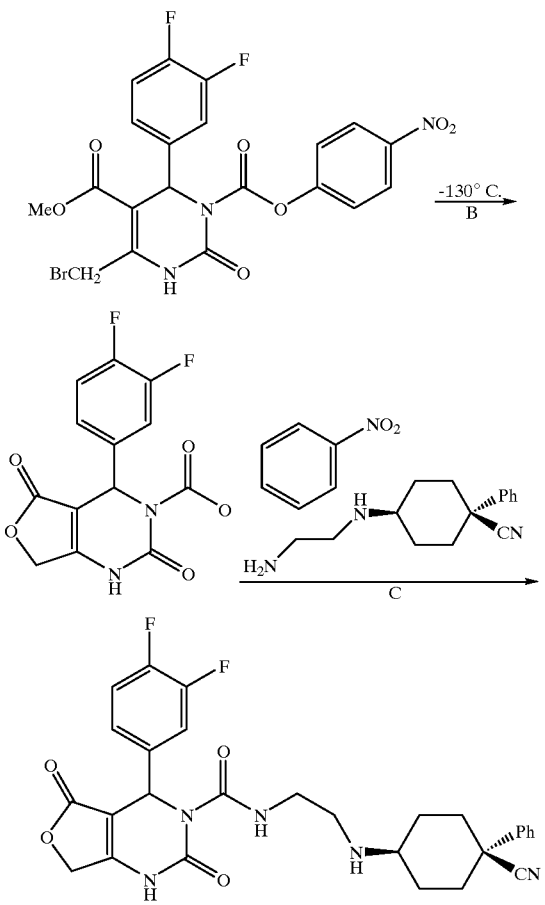

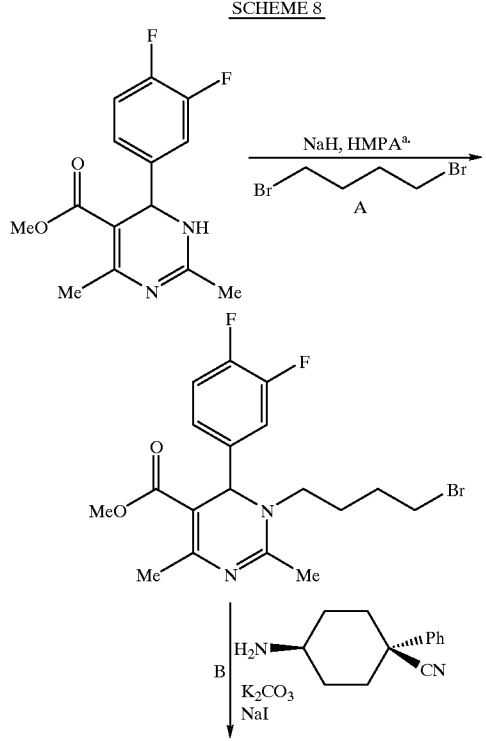

SCHEME 8

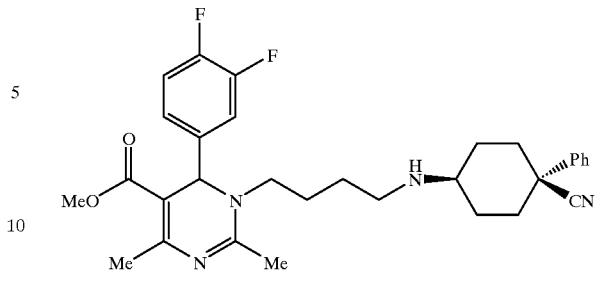

a. HMPA = hexamethylphosphoramide

Similar compounds may be produced by substitution of the 1,4-dibromobutane with other dibromoalkanes, including branched compounds in order to produce the alkyl-linked cycloalkylamine derivatives of the subject dihydropyrimidines.

What is claimed is:

1. A compound having the structure:

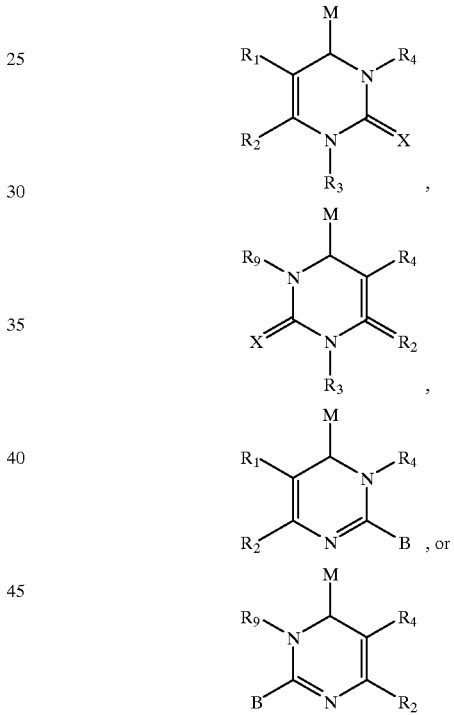

where M has the structure

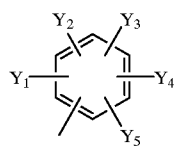

wherein each of $Y_1$, $Y_2$, $Y_3$, $Y_4$ and $Y_5$ independently is —H; straight chained or branched $C_1$–$C_7$ alkyl, monofluoroalkyl, or polyfluoroalkyl; straight chained or branched $C_2$–$C_7$ alkenyl or alkynyl; $C_3$–$C_7$ cycloalkyl, monofluorocycloalkyl, polyfluorocycloalkyl, or cycloalkenyl; —F, —Cl, —Br, or —I; —$NO_2$; —$N(R_3)_2$; $N_3$; —CN; —$OR_3$;

—OCOR$_3$; —COR$_3$; —CON(R$_3$)$_2$; or —CO$_2$R$_3$; or wherein two of Y$_1$, Y$_2$, Y$_3$, Y$_4$ and Y$_5$ are present on adjacent carbon atoms and together constitute a methylenedioxy group;

where R$_1$ is —H; —NO$_2$; —CN; straight chained or branched C$_1$–C$_7$ alkyl, monofluoroalkyl, or polyfluoroalkyl; straight chained or branched C$_2$–C$_7$ alkenyl or alkynyl; C$_3$–C$_7$ cycloalkyl, monofluorocycloalkyl, polyfluorocycloalkyl, or cycloalkenyl; —N(R$_3$)$_2$; —OR$_3$; —(CH$_2$)$_p$OR$_3$; —COR$_3$; —CO$_2$R$_3$; or —CON(R$_3$)$_2$; wherein p independently is an integer from 1 to 7 inclusive;

where R$_2$ is —H; straight chained or branched C$_1$–C$_7$ alkyl, hydroxyalkyl, alkoxyalkyl, aminoalkyl, monofluoroalkyl, or polyfluoroalkyl; straight chained or branched C$_2$–C$_7$ alkenyl or alkynyl; C$_3$–C$_7$ cycloalkyl, monofluorocycloalkyl, polyfluorocycloalkyl, or cycloalkenyl; C$_3$–C$_{10}$ cycloalkyl-C$_1$–C$_{10}$-alkyl, C$_1$–C$_{10}$ cycloalkyl-C$_1$–C$_{10}$-monofluoroalkyl or C$_3$–C$_{10}$ cycloalkyl-C$_1$–C$_{10}$-polyfluoroalkyl; —CN; —CH$_2$XR$_3$, —CH$_2$X(CH$_2$)$_p$NHR$_3$, —(CH$_2$)$_n$NHR$_3$, —CH$_2$X(CH$_2$)$_p$N(R$_3$)$_2$, —CH$_2$X(CH$_2$)$_p$N$_3$, or —CH$_2$X(CH$_2$)$_p$NHCXR$_7$; or —OR$_3$; wherein n independently is an integer from 0 to 5 inclusive and p is as defined above;

where each R$_3$ independently is —H; straight chained or branched C$_1$–C$_7$ alkyl, monofluoroalkyl, or polyfluoroalkyl; straight chained or branched C$_2$–C$_7$ alkenyl or alkynyl; C$_3$–C$_7$ cycloalkyl, monofluorocycloalkyl, polyfluorocycloalkyl, or cycloalkenyl; —(CH$_2$)$_p$OH; or —(CH$_2$)$_p$CO$_2$R$_8$; wherein p is as defined above, and R$_8$ is —H; straight chained or branched C$_1$–C$_7$ alkyl, monofluoroalkyl, or polyfluoroalkyl; straight chained or branched C$_2$–C$_7$ alkenyl or alkynyl; C$_3$–C$_7$ cycloalkyl, monofluorocycloalkyl, polyfluorocycloalkyl, or cycloalkenyl;

where R$_4$ has the structure

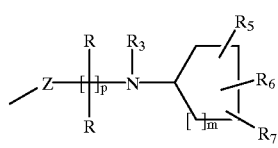

wherein Z is C$_2$–C$_7$ alkenyl or alkynyl, CH$_2$, O, CO, CO$_2$, CONR$_3$CO, CONR$_3$, S, SO, SO$_2$, or NR$_3$; m is an integer from 0 to 3 inclusive; p is as defined above; R independently is —H; —F; straight chained or branched C$_1$–C$_7$ alkyl, monofluoroalkyl, or polyfluoroalkyl; straight chained or branched C$_1$–C$_7$ alkenyl or alkynyl; —N(R$_3$)$_2$; —NO$_2$; —CN; —CO$_2$R$_3$; —(CH$_2$)$_p$OR$_3$; or —OR$_3$; R$_3$ is as defined above; R$_5$ and R$_6$ each independently is —H; —F; —Cl; —Br; —I; —CO$_2$R$_3$; —COR$_3$; —CON(R$_3$)$_2$; —CN; —NO$_2$; —N(R$_3$)$_2$; —OR$_3$; straight chained or branched C$_1$–C$_7$ alkyl, C$_1$–C$_7$ monofluoroalkyl, C$_1$–C$_7$ polyfluoroalkyl, C$_2$–C$_7$ alkenyl, C$_2$–C$_7$ alkynyl, C$_3$–C$_7$ cycloalkyl, or C$_3$–C$_7$ cycloalkenyl; wherein the alkyl, monofluoroalkyl, polyfluoroalkyl, alkenyl, alkynyl, cycloalkyl, or cycloalkenyl is unsubstituted or substituted with —H, aryl, or heteroaryl; aryl or heteroaryl; and wherein the aryl or heteroaryl is unsubstituted or substituted with —H, —F, —Cl, —Br, —I, —NO$_2$, —CN, —N(R$_3$)$_2$, —OR$_3$, —COR$_3$, —CO$_2$R$_3$, or —CON(R$_3$)$_2$; straight chained or branched C$_1$–C$_7$ alkyl, monofluoroalkyl, or polyfluoroalkyl; straight chained or branched C$_2$–C$_7$ alkenyl or alkynyl; C$_3$–C$_7$ cycloalkyl, monofluorocycloalryl, polyfluorocycloalkyl, or cycloalkenyl; and R$_7$ is —H; straight chained or branched C$_1$–C$_7$ alkyl, hydroxyalkyl, aminoalkyl, alkoxyalkyl, monofluoroalkyl, or polyfluoroalkyl; straight chained or branched C$_2$–C$_7$ alkenyl or alkynyl; C$_3$–C$_7$ cycloalkyl, monofluorocycloalkyl, polyfluorocycloalkyl, or cycloalkenyl; —CN; —CO$_2$R$_3$; —COR$_3$; —CON(R$_3$)$_2$; or —OR$_3$; where aryl or heteroaryl is benzyl, benzoyl, naphthyl, phenyl, pyridyl, thienyl, furanyl, pyrazinyl, pyrrolyl, indolyl, imidazolyl, benzfurazanyl, benzo[b]furanyl, quinolinyl, benzimidazolyl, or 2-keto-1-benzimidazolinyl;

where R$_9$ is —H; —CN; straight chained or branched C$_1$–C$_7$ alkyl, monofluoroalkyl, or polyfluoroalkyl; straight chained or branched C$_2$–C$_7$ alkenyl or alkynyl; C$_3$–C$_7$ cycloalkyl, monofluorocycloalkyl, polyfluorocycloalkyl, or cycloalkenyl; —N(R$_3$)$_2$; —OR$_3$; —(CH$_2$)$_p$OR$_3$; —COR$_3$; —CO$_2$R$_3$; or —CON(R$_3$)$_2$;

where X is S; O; or NR$_3$; and where B is —H; straight chained or branched C$_1$–C$_7$ alkyl, monofluoroalkyl, polyfluoroalkyl, or alkoxy; straight chained or branched C$_2$–C$_7$ alkenyl; —SCH$_2$C$_6$H$_4$OR$_3$; —(CH$_2$)$_n$C$_6$H$_5$; —CH$_2$X(CH$_2$)$_n$NHR$_3$; —(CH$_2$)$_n$NHR$_3$, or —OR$_3$;

or a pharmaceutically acceptable salt thereof.

2. The compound of claim 1, wherein the compound comprises the (+) enantiomer.

3. The compound of claim 1, wherein the compound comprises the (−) enantiomer.

4. The compound of claim 1, wherein the compound has the structure:

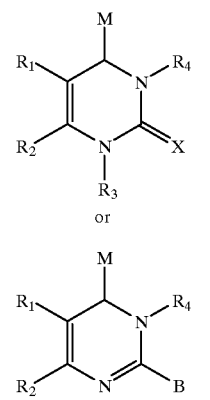

5. The compound of claim 1, wherein R$_4$ is

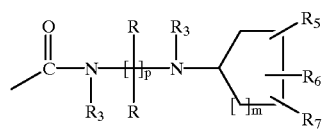

and p is 2, 3, or 4.

6. The compound of claim 1, wherein $R_4$ is

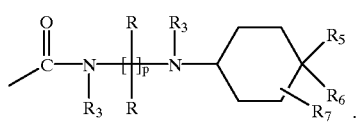

7. The compound of claim 6, having the structure:

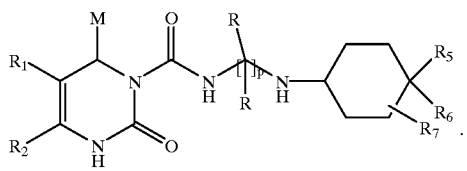

8. The compound of claim 7, wherein M is polyfluorophenyl and $R_5$ is substituted or unsubstituted phenyl or pyridyl.

9. The compound of claim 8, wherein $R_1$ is —$CO_2CH_3$, —$COCH_3$, or —$CONH_2$; $R_2$ is —$CH_2OCH_3$, methyl or ethyl; and $R_6$ is H, —CN, or $CO_2CH_3$.

10. The compound of claim 6, wherein the compound is selected from the group consisting of:

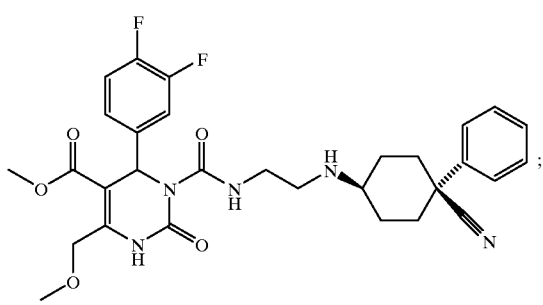

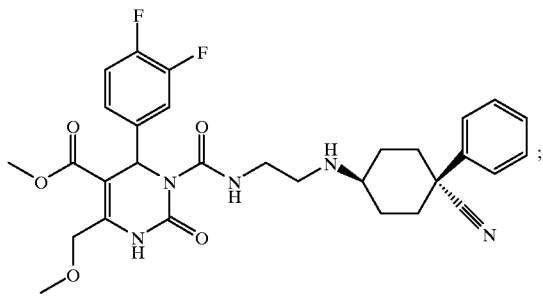

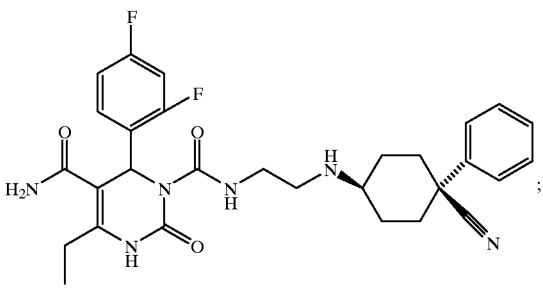

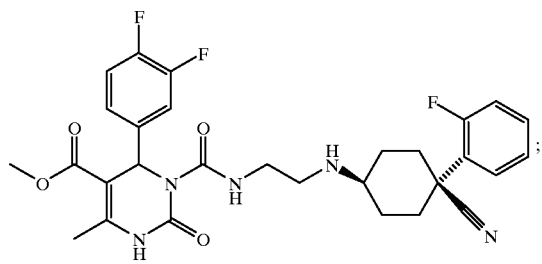

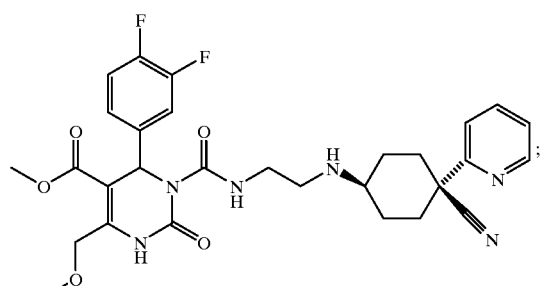

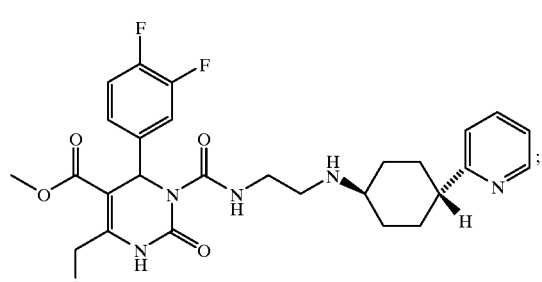

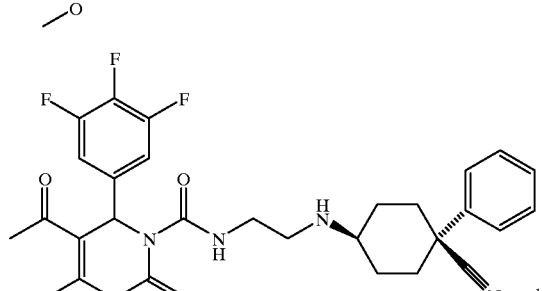

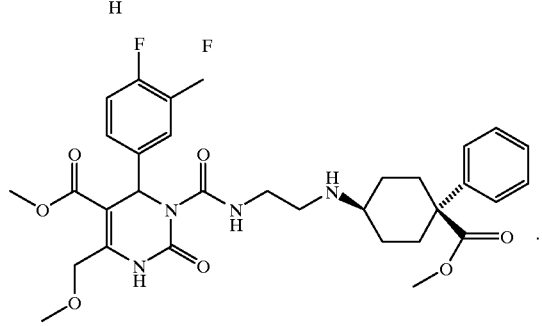

11. The compound of claim 10, wherein the compound is the (+) enantiomer.

12. The compound of claim 10, wherein the compound is the (−) enantiomer.

13. A composition comprising a therapeutically effective amount of the compound of claim 1 and a pharmaceutically acceptable carrier.

14. The composition of claim 13, wherein the amount is from about 0.01 mg to about 500 mg.

15. The composition of claim 14, wherein the amount is from about 0.1 mg to about 60 mg.

16. The composition of claim 15, wherein the amount is from about 1 mg to about 20 mg.

17. The composition of claim 13, wherein the carrier is a liquid and the composition is a solution.

18. The composition of claim 13, wherein the carrier is a solid and the composition is a tablet.

19. The composition of claim 13, wherein the carrier is a gel and the composition is a suppository.

\* \* \* \* \*